United States Patent [19]

Richards et al.

[11] Patent Number: 5,270,201
[45] Date of Patent: Dec. 14, 1993

[54] ARTIFICIAL CHROMOSOME VECTOR

[75] Inventors: Eric J. Richards, Lloyd Harbor, N.Y.; Frederick M. Ausubel, Newton, Mass.

[73] Assignee: The General Hospital Corporation, Boston, Mass.

[21] Appl. No.: 860,585

[22] Filed: Mar. 30, 1992

Related U.S. Application Data

[63] Continuation of Ser. No. 742,554, Aug. 9, 1991, abandoned, which is a continuation of Ser. No. 404,525, Sep. 8, 1989, abandoned, which is a continuation-in-part of Ser. No. 172,467, Mar. 24, 1988, abandoned.

[51] Int. Cl.$^5$ .................... C12N 5/10; C12N 1/19; C12N 15/11; C12N 15/82
[52] U.S. Cl. ........................ 435/240.4; 435/252.33; 435/320.1; 435/240.1; 435/254.2; 536/23.1
[58] Field of Search ............... 435/172.3, 252.3, 320.1, 435/240.4, 252.33, 256, 240.1; 536/27, 23.1

[56] References Cited

FOREIGN PATENT DOCUMENTS 048081 3/1982 European Pat. Off. .
WO86/00089 1/1986 PCT Int'l Appl. .

OTHER PUBLICATIONS

Ariga et al. (1987) Mol Cell Biol 7:1-6.
Blackburn et al. (1984) in Ann Rev Biochem 53:163-94.
Pouivels et al. eds in Cloning Vectors (1985) Elsevier, N.Y.
Wang-Gabs et al. (1984) PNAS 81:4884-4888.
Schechtman et al. (1987) Mol Cell Biol 7:3168-77.
Saiga et al. (1985) EMBO J. 4:799-804.
Rao et al. (1986) Nucleic Acids Res. 14:7504.
CA 63286j vol 104(9) p. 192 (Babel et al).
CA 1603b vol. 104(1) p. 149 (Mitchell et al).
CA 160421d vol. 89(19) p. 323 (Rubin et al.).
CA 117334y vol. 103(15) p. 189 (Barnes et al.).
Jongsma, M., et al., Plant Molec. Biol. 8:383-394 (1987).
Yu, G-L. et al., "In vivo alteration of telomere sequences and senescence caused by mutated Tetrahymena telomerase RNAS," Nature 344:126-132 (1990).
Lustig, A. J. et al., "Involvement of the Silencer and UAS Binding Protein RAP1 in Regulation of Telomere Length," Science 250:549-553 (1900).
Yu, X-M. et al., "The telomeres of Tetrahymena ribosomal DNA are not sufficient for stabilizing linear DNA in Xenopus oocytes," Gene 56:313-319 (1987).
Rubin, G. M. Cold Spring Harbor Symp. Quant. Biol. 42:1041-1046 (1978).
Barnes, S. R., et al., Chromosoma 92:185-192 (1985).
Mitchell, A. R., et al., Chromosoma 92:369-377 (1985).
Dunn, B. et al., Cell 39:191-201 (1984).
Allshire, R. C. et al., Nature 332:656-659 (1988).
Zakian, V. A., Annu. Rev. Genet. 23:579-604 (1989).
Cech, T. R. et al., Nature 332:777-778 (1988).
Ganal, M. W. et al., The Plant Cell 3:87-94 (1991).
Lozano, R. et al., Heredity 64:185-195 (1990).
Broun, P. et al., Proc. Nat'l. Acad. Sci. USA 89:1354-1357 (1992).
Roberts, Leslie, Science 240:982-983 (1988).
Richards, E. J. et al., Cell 53:127-136 (1988).
Ponzi, M., et al. The EMBO Journal 4:2991-2995 (1985).
Murray et al., Nature 305:189-193 (1983).
Clarke et al., Nature 287(9):504-509 (1980).
Stinchcomb et al., J. Molec. Biol. 158:157-179 (1982).
Zabel, P., et al., NATO ASI Series, Series A 83:609-624 (1985).

(List continued on next page.)

Primary Examiner—Richard A. Schwartz
Assistant Examiner—Philip W. Carter
Attorney, Agent, or Firm—Sterne, Kessler, Goldstein & Fox

[57] ABSTRACT

The present invention relates to a recombinant DNA molecule which contains the telomere and, optionally, the centromere of a higher eukaryote, particularly a plant, the telomere itself, the centromere itself, a method of producing a polypeptide in a recipient cell which utilizes said recombinant DNA molecule, host cells transformed with said recombinant molecule, and uses for said recombinant molecule.

25 Claims, 19 Drawing Sheets

OTHER PUBLICATIONS

Szostak, J. W., *Cold Spring Harbor Symp. Quant. Biol.* 47:1187-1194 (1983).
Roth et al., *Mol. Cell Biol.* 3(11):1898-1908 (1983).
Zabel et al., *Molec. Form. & Func. of Plan Genome* (Plenum Press), pp. 609-624 (1985).
Blackburn et al., *Cell* 36:447-457 (1984).
Shampay et al., *Nature* 310:154-157 (1984).
Allshire et al., *Cell* 50:391-403 (1987).
Thomas et al., *Cell* 44:419-428 (1986).
Smithies et al., *Nature* 317:230-234 (1985).
Stinchcomb et al., *Proc. Natl. Acad. Sci. USA* 77(8):4559-4563 (1980).
Murray et al., *Cell* 45:529-536 (1986).
Burke et al., *Science* 236:806-812 (1987).
Ausubel et al., *Curr. Prot. Molec. Biol.* (New York: John Wiley & Sons, 1987).
Potrykus et al., *Plant Molec. Biol. Rptr.* 3:117-128 (1985).
Perrot et al., *Mol. Cell. Biol.* 7:1725-1730 (1987).
Murray et al., *Sci. Amer.* pp. 62-68, Nov. 1987.
Pang et al. *Biotech* 5:1177-1181 (1987).
Blackburn, E. H., *Trends in Genetics* 1:8-12 (1985).
Szostak et al., *Cell* 29:245-255 (1982).
Appels et al., *Chromosoma* (Berl.) 84:265-277 (1981).
Richards et al., *Cell* 53:127-136 (1988).
Forney, J., *Nucl. Acids Res.* 15:9145-9148 (1987).
Johnson, E. M., *Cell* 22:875-886 (1980).

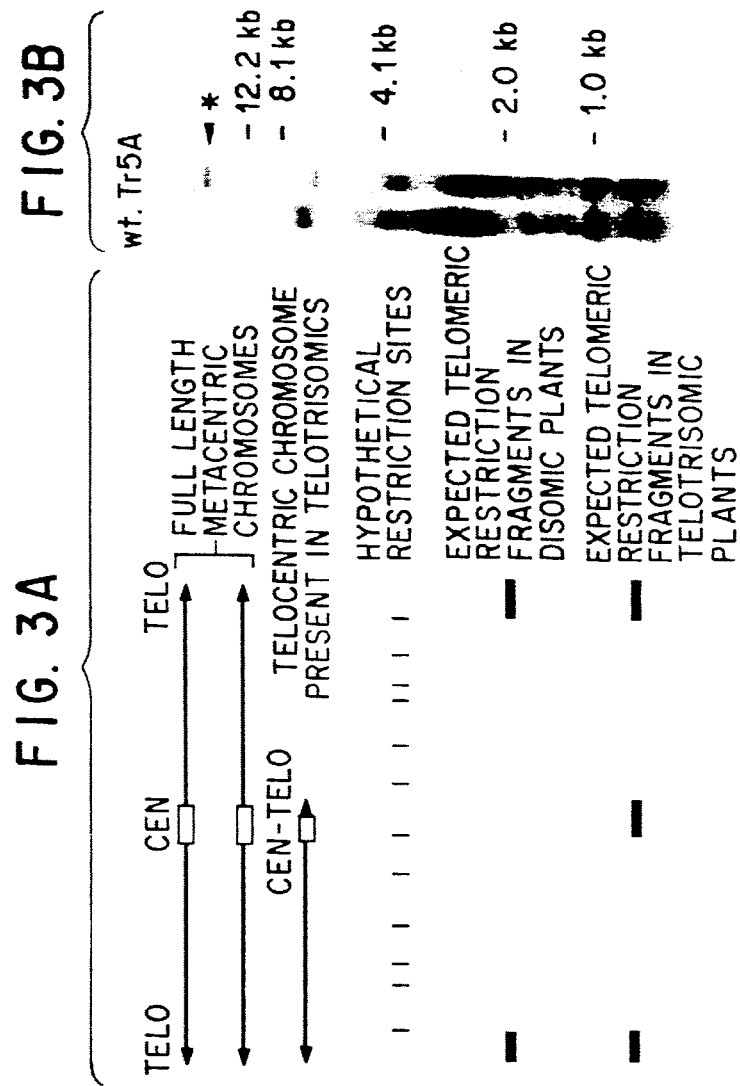

```
                    1/2 HincII
AAGCTTGGGCTGCAGGTCA CCCTAAA CCCTAAA CCCTAAA
CCCTAAA CCCTAAA CCCTAAA CCCTAAA CCCTAAA
CCCTAAA CCCTAAA CCCTAAA CCCTAAA CCCTAAA
CCCTAAA CCCTAAA CCCTAAA CCCTAAA CCCTAAA
CCCTAAA CCCTAAA CCCTAAA CCCTAAA CCCTAAA
CCCTAAA CCCTAAA CCCTAAA CCCTAAA CCCTAAA
CCCTAAA CCCTAAA CCCTAAA CTCTAAA CTCTAAA
CCCTAAA CCCTAAA CCCTAAA CCCTAAA CCCTAAA
CCCTAAA CCCTAAA CCCTAAA CCCTAAA CCCTAAA
CCCTAAA CCCTAAA CCCTAAA CCCTAAA CCCTAAA
CCCTAAA CCCTAAA CCCTAAA CCCTAAA CCCTAAA
CCCTAAA CCCTAAATAAAGCGCTGTGGGATCcccGGGCGA
                                    MboI
```

FIG. 4

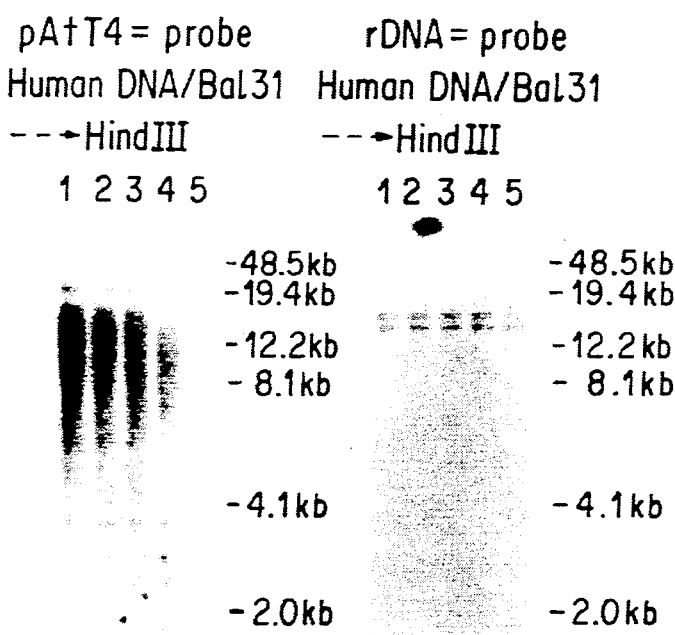

Making small minichromosomes: Fragmenting full length chromosomes through resolution of integrated telomere inverted repeats Step One: Start with a full length chromosome

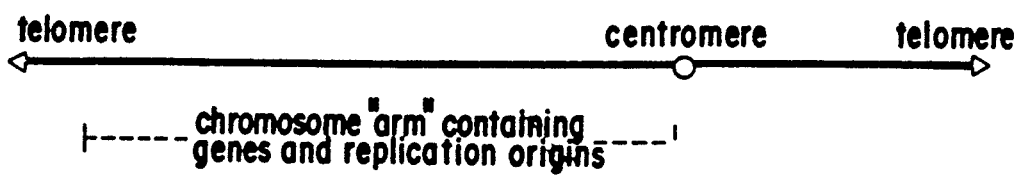

Step Two: Construct a telomere inverted repeat, flanked by two different drug resistance markers in T-DNA vector

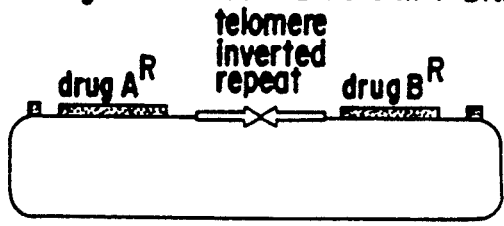

Step Three: Intoduce the telomere inverted repeat construct into a plant chromosome

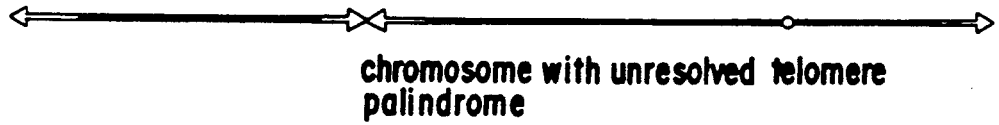

chromosome with unresolved telomere palindrome

Step Four: Screen for resolution of the telomere inverted repeat by Southern blotting experiments

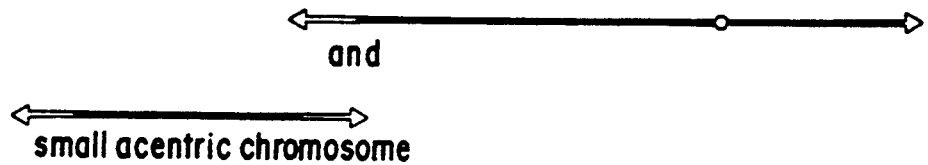

Step Five: Isolate small acentric chromosome; subclone to delimit ARS

Functional selection for Plant ARSs: Shotgun cloning

Step One: Start with a cloning vector of this general design

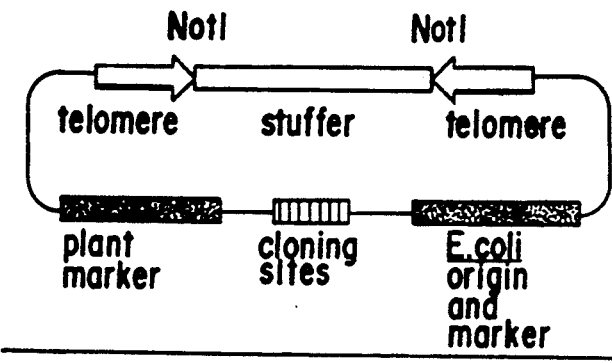

Step Two: Construct a plant genomic library in this vector: maintain in E. coli

Step Three: Prepare plasmid DNA from this library; linearize with NotI

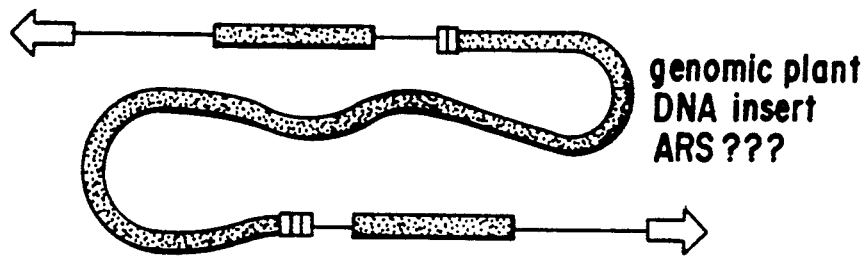

genomic plant DNA insert ARS???

Step Four: Direct DNA transformation into plant protoplasts; select transformants as callus Step Five: Screen for instability of plant marker under nonselective growth, evidence for extrachromosomal maintenance Step Six: Prepare extrachromosomal DNA and recover plant ARS

FIG.9

Cloning Plant Centromeres using Telomeric probes and Telotrisomic mutants

Step One: Prepare DNA from telotrisomic mutant and normal disomic plants

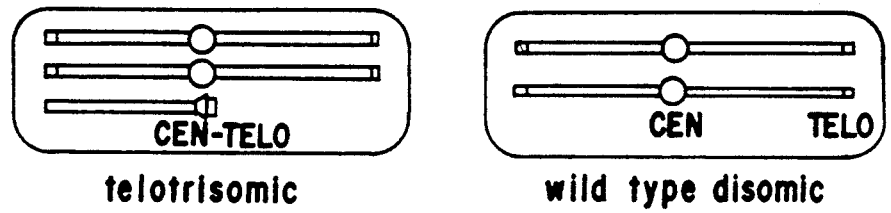

telotrisomic      wild type disomic

Step Two: Do a genomic Southern blot, probe with radiolabeled telomere; Look for RFLPs

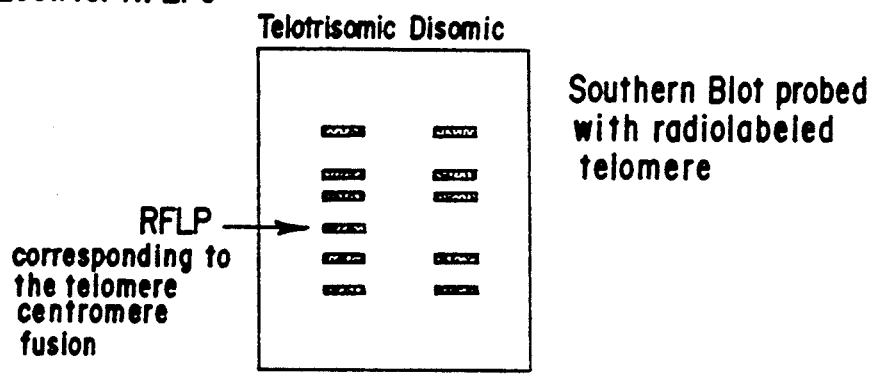

Southern Blot probed with radiolabeled telomere

RFLP corresponding to the telomere centromere fusion

Step Three: Purify end-repaired, restricted genomic telotrisomic DNA corresponding to CEN-TELO RFLP; construct a library in a yeast ARS CEN vector

Step Four: Screen the library using the telomere probe to find clones containing the CEN-TELO fusion fragment

Step Five: Test putative CEN clones: Southerns of all telotrisomics, Mitotic stabilization Dicentric assay, DNA binding protein analysis

PLANT ARTIFICIAL CHROMOSOMES
A. E. coli/PLANT CIRCULAR SHUTTLE VECTOR
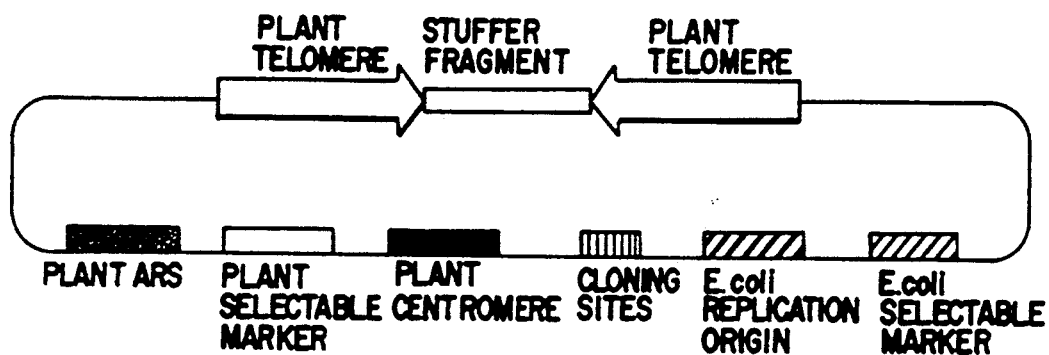
B. YEAST/PLANT CIRCULAR SHUTTLE VECTOR
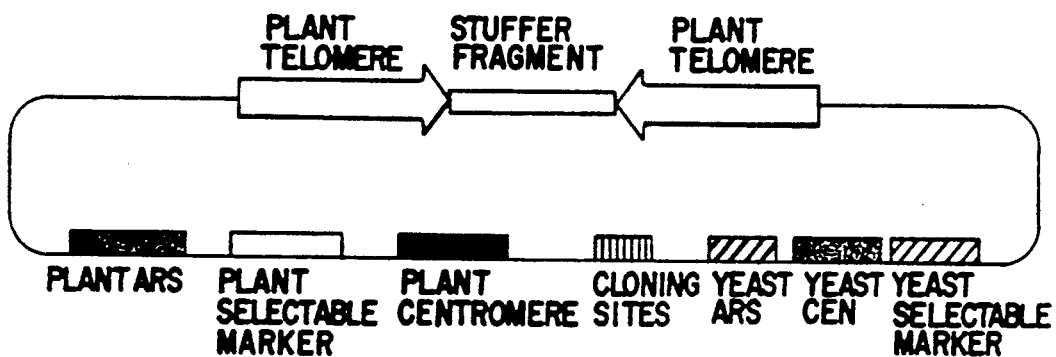
C. YEAST/PLANT LINEAR SHUTTLE VECTOR
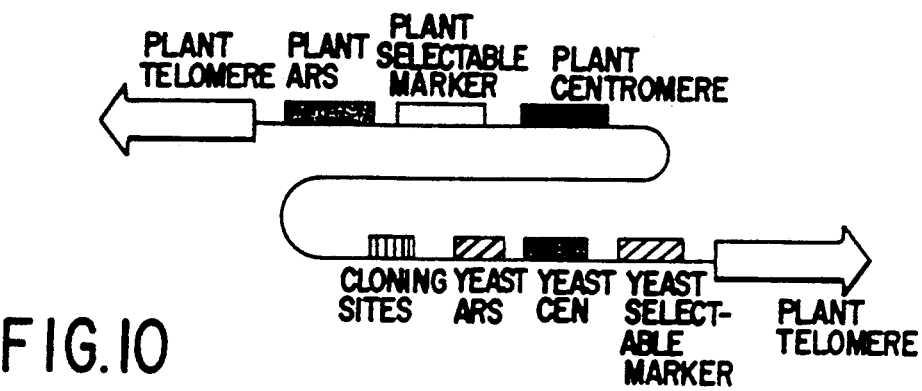
FIG. 10

Ara DNA/Bal31
- - -HindIII
1 2 3 4 5

—12.2kb
—7.1kb
—4.1kb
—2.0kb
—1.0kb
—0.5kb

High Stringency

Ara DNA/Bal31
- - -HindIII
1 2 3 4 5

12.2kb-
7.1kb-
4.1kb-
2.0kb-
1.0kb-
0.5kb-

Low Stringency

```
Plurality:   1  AAGCTTTGAGAATCAAGAAGAAGCTTTG.TAGCGGATTTGTGTAGTCAAATATGACTAGAGATGCTTTGTGTATTATTGAGCATAAGAACTAGAACCGCAACCA  100
pAtT20:         .....................G.G...........................A..C.......T..................T......G
pAtT24:         ..................TG....AT..........A..C....T............CG.............A..................
pAtT25:         ...........................C...............T...............................................

Plurality: 101  GATTCCGGAAGCCTAAAAGTAGGATTTGGTTTAAAGTTTGGGATCTATGGTTTAAGTTTTTTTGGGTTTAGGTTAAAGGTTTAGGGTTTAGGTTTAAGGTTTAAG  200
pAtT20:         .....................A....G............................................T.................
pAtT24:         .C....AA............A...........A.........GA....................----------................
pAtT25:         ....................................................T..............................

Plurality: 201  GGTTTAGGGTTTAAGGGTTTAGGGTTTAAGAGTTTATGGTTTAGGGTTTAGGGTTTAGGGTTTAGGGTTT..GGGTAGGAT  300
pAtT20:         .................................................G..A................TT....A....
pAtT24:         .......G..C.A......................G...A....T.....T.A..T.A..TTA...........—.....
pAtT25:         A.......A............................T...........C........T......A..........AG.T.T.
```

FIG. 14 — Chromosome 1 Genetic Map / RFLP Map

```
  1 AGCTTCTTCATGATTCTCAAAGATTTGATGGTGAACCCAAAGTTCTTAACAGTTTTGGTTTTTGAATTGTATAACAGAAAGCACTACTACAAGAAA   100
101 ACACGGTTTTACGACCACATCTGACGAGTGTACAAGTAGTCGTAATATTAAATGACTATAGGCGACAAATCTACGACTAAAATAAAA           200
201 GGGACGTTCCGTAGTCGCTAAATGACGACTGTGTTTTAATAGTCGTTCAAGTAGTCGTTAGATAACGACTAAGTTGCGACTATAAGTCGGAGAATTA  300
301 AGAGTCGCTAATAAGTCGTTAAAATTGTAACAATAATCAAAGAATTTTTATAGTGTATAGTTTTGTGTATACTAAGTAAAATTAGATATGCTAAATTA  400
401 GACTATTAGTTTTTGTAATTGTTAAGATATAAGTTAGAATTATAACATATATTTCAGTTCAAAGCATTATTTTAAAAATGCATTCTTTAAACAATTGTACAAA 500
501 GTATATATATATATATAGTGATTGAACATTATTTTGGTATGAAGGGTTAATCACCAAAATAACCTATAATTTGTAAAAACCTATGATTTTGTTAA   600
601 AAATGCACTATCTTTATTAAAAATTGTACAAAGTATATATCACTCTAATTAATAAATTAAAAAGGATATATATTAATGGATATATAGTGATTGAA    700
701 CATTGTTTTGGTATGATGAAGGGTTAATCACATAAATAACTTGTTGTTTTGGATATAGACCAAAGTTATGAAAACCTATGATTATTTAAAAAATTAATAAACAC 800
801 TGCGACTGAATAACGACTAATAAGCGACTACAATCAAAACATTGGGCTGAATTAAAACCGAGAAAACTATCGCGGCCAAAATTAACGAGGCCCAAACA    900
901 AAGCCCAAACATTGTGTCGATTAGCGAGGATGAAGAACGAGAATGAGGAACCCTAATTCATTCTTCTCTGCCTCTCTCCACTCTCTCTCTTGTTCTTC  1000
1001 GATTCACCCTGAATCTTCATCTCTCTCTTCGTTCTTCAATCCTCCTCAATCTTCATCAATGTTCTCCTTCTGCTATCTTTTTCTTCGAATCTCT      1100
1101 CGGATCTCTCACTTTCAGAAGAGTGTCTCCTCAGGGTTGCAAACAAGGTCGATTCGATGCCTCTAGCTAAGCGAGGAAGGAAGAGAAAAATGGAA     1200
```

FIG.16A

```
1201  CCCAATGTTACTCAGAGAGCTGGAGCCTCTACTCCAATTACAGGGAAACGAATAAACCCTCTACTCCTCAATACAACTTTACGCCGGCGGGACAACAATC  1300
1301  CTCCACCTCAGTCATCCCAAGAGCGAGTCCGGGTTCAACCCCAACTAGCAAGGTCATTCACTCCCGAGTCTCTGACTATCCACCTCCGCAAGCCCTTT    1400
1401  CCAGAACTCCTCTAATCGTGAAGTCCCTGTACCTCTTTTGTTAGAAGAAGTCAGAACGAGGCATCTAATCGATTCCACAACAAGATCCTCCAGGT        1500
                                                                                          SacI
1501  TCTCCACTTCAGAACTCTCATGCAAGTCAACCATCTTCCAAGGCAACAACTTCCACGAACCTGTGGCTGATGTTACCGGAGCTCCGGGAGGACAGTT     1600
1601  TGAGGGCTTGAAATGATGTGCTTCAAAAGCCTGGCCGTGAGGCGTGGACCATGTCGCTTCTCCCACACCGATGCGAAAAATAACTTGGTAAGTACTTAG   1700
1701  ATATGTCTTGGTTAGTAGTCTGGAATCTCATGAGAAATGTTTGTTGTGAGTGTATTGAGTGTAGTCGTGCGAGTGTCTAGTATAAATGTGTC          1800
1801  TTGTGTATTGATTGAAGTAGTGATTAGAGTCTGAAGTAGATGTTGATTGTGATTGGAGTGTATTGGAAGGTAGAGTGGAACCTGAAGGTTGTGTTGAGTGTTTGATT 1900
1901  AGAGTCTGAATTAGAGTGTCTTAAGTGTATTGATTGATTATTAGAAGTGTCTTAAGTGTTTGTTTGTTGAATTAGAGT                       2000
2001  CCGATGCAAAACACAACTTATTAAGTGTCTTGTTTGATGAATGAATGTGTCTTTGTCTTAAGCGTGTGTTTGTTTGTTGAATTAGAGTGTCTAAGTG     2100
```

FIG.16B

ARTIFICIAL CHROMOSOME VECTOR

CROSS REFERENCE TO RELATED APPLICATION

This application is a continuation of application Ser. No. 07/742,554, filed Aug. 9, 1991, now abandoned, which is a continuation of application Ser. No. 07/404,525, filed Sep. 8, 1989, now abandoned, which is a continuation-in-part of U.S. application Ser. No. 07/172,467 filed Mar. 24, 1988, now abandoned.

FIELD OF THE INVENTION

This invention relates to the field of plant recombinant genetics.

BACKGROUND OF THE INVENTION

The development of recombinant DNA techniques has opened up the possibility of making specific changes in an organism's genetic makeup. Alteration of genetic endowment can lead to the development of useful strains of microorganisms, and more productive varieties of domesticated plants and animals. For example, insect resistant plants have recently been produced by the addition of a bacterial gene which instructs the recipient plants cells to produce a protein toxic to certain types of insects (see Vaeck, et al., *Nature* 328:33 (1987)). Manipulation of plant species through genetic engineering will become an important complement to classical breeding techniques in the development of plant varieties with new traits, such as improved nutritional quality, productivity, disease resistance, and drought and salinity tolerance.

Genetic engineering involves two basic processes: (1) isolation and propagation of new or altered genes (molecular cloning), and (2) the introduction of these genes into the recipient organism in a form that allows the introduced genetic information to be read (i.e., expressed) and transmitted to successive generations. The basic techniques of molecular cloning are well established, but the necessary tools for accomplishing the efficient introduction and expression of new genetic information in higher eukaryotic organisms are still limited.

Two general approaches are used to introduce new genetic information into cells, a procedure commonly referred to as "genetic transformation." One approach is to introduce the new genetic information as part of another DNA molecule, referred to as a "vector," which can be maintained as an independent unit (i.e., an episome) apart from the chromosomal DNA molecule(s). Episomal vectors contain all the necessary DNA sequence elements required for DNA replication and maintenance of the vector within the cell. Many episomal vectors are available for use in bacterial cells (for example, see Maniatis, T., et al., *Molecular Cloning: A Laboratory Manual* (Cold Spring Harbor, 1982)). However, only a few episomal vectors that function in higher eukaryotic cells have been developed. The available higher eukaryotic episomal vectors are based on naturally occurring viruses and most function only in mammalian cells. In higher plant systems there are no known double-stranded DNA viruses that replicate through a double-stranded intermediate upon which an episomal vector can be based. Although an episomal plant vector based on the Cauliflower Mosaic Virus has been developed, its capacity to carry new genetic information is limited (Brisson et al., *Nature* 310:511 (1984)).

The other general method of genetic transformation involves integration of the introduced DNA sequences into the recipient cell's chromosomes which permits the new information to be replicated and partitioned to the cell's progeny as a part of the natural chromosomes. The most common form of integrative transformation is called "transfection" and is frequently used in mammalian cell culture systems. Transfection involves introduction of relatively large quantities of deproteinized DNA into cells. The introduced DNA usually is broken and joined together in various combinations before it is integrated at random sites into the cell's chromosome (see, for example Wigler, et al., *Cell* 11:223 (1977)). A common problem with this procedure is the rearrangement of introduced DNA sequences (see Shingo, K., et al., *Mol. Cell. Biol.* 6:1787 (1986)). A more refined form of integrative transformation can be achieved by exploiting naturally occurring viruses that integrate into the host's chromosomes as part of their life cycle (e.g., retroviruses) (see Cepko, C., et al., *Cell* 37:1053 (1984)).

The most common genetic transformation method used in higher plants is based on the transfer of bacterial DNA into plant chromosomes that occurs during infection by the phytopathogenic soil bacterium Agrobacterium (see Nester et al., *Ann. Rev. Plant Phys.* 35:387–413 (1984)). By substituting genes of interest for the naturally transferred bacterial sequences (called T-DNA), investigators have been able to introduce new DNA into plant cells. However, even this more "refined" integrative transformation system is limited in three major ways. First, DNA sequences introduced into plant cells using the Agrobacterium T-DNA system are frequently rearranged (see Jones, et al., *Mol. Gen. Genet.* 207:478 (1987)). Second, the expression of the introduced DNA sequences varies between individual transformants (see Jones et al., *EMBO J.* 4:2411–2418 (1985)). This variability is presumably caused by rearranged sequences and the influence of surrounding sequences in the plant chromosome (i.e., position effects). A third drawback of the Agrobacterium T-DNA system is the reliance on a "gene addition" mechanism: the new genetic information is added to the genome (i.e., all the genetic information a cell possesses) but does not replace information already present in the genome. While gene addition is suitable for many applications, the ability to actually replace a specific gene with an altered copy via homologous recombination (i.e., recombination between DNA of the same or a similar sequence) would be extremely useful. Gene replacement in mammalian cells using a transfection protocol has been attempted, but the procedure is inefficient (approximately 1 out of every 1000 transformed cells underwent a gene replacement event in Thomas et al., *Cell* 44:419 (1986); see also Smithies, et al., *Nature* 317:230 (1985)).

The present invention discloses linear episomal transformation vectors, based on natural chromosomes, that can replicate and be stably maintained in higher plant cells. These artificial plant chromosome vectors will provide a versatile tool for genetic transformation of plant species and solve many of the problems associated with present DNA transformation technology. In addition, development of artificial plant chromosome vectors will facilitate the construction of artificial chromosomes that can function in other higher eukaryotic cells.

Artificial chromosomes are man-made linear DNA molecules constructed from essential cis-acting DNA sequence elements that are responsible for the proper replication and partitioning of natural chromosomes (see Murray et al., *Nature* 301:189–193 (1983)). These essential elements are: (1) Autonomous Replication Sequences (ARS) (have properties of replication origins, which are the sites for initiation of DNA replication), (2) Centromeres (site of kinetochore assembly and responsible for proper distribution of replicated chromosomes at mitosis and meiosis), and (3) Telomeres (specialized structures at the ends of linear chromosomes that function to stabilize the ends and facilitate the complete replication of the extreme termini of the DNA molecule).

At present, these essential chromosomal elements have been isolated only from lower eukaryotic species. ARSs have been isolated from the unicellular fungi *Saccharomyces cerevisiae* (brewer's yeast) and *Schizosaccharomyces pombe* (see Stinchcomb et al., *Nature* 282:39–43 (1979) and Hsiao et al., *J. Proc. Natl. Acad. Sci. USA* 76:3829–3833 (1979)). ARSs behave like replication origins allowing DNA molecules that contain the ARS to be replicated as an episome after introduction into the cell nuclei of these fungi. Although plasmids containing these sequences replicate, they do not segregate properly.

Kinetochores are complex nucleo-protein structures, located at the centromeres, responsible for the proper partitioning of the chromosomes during mitosis and meiosis. The DNA component of the kinetochore, or centromeric DNA, provides the cis-acting signals specifying the location of kinetochore assembly, and controlling sister chromatic separation at mitotic and meiotic anaphase.

Functional centromeric (CEN) sequences have been purified from *S. cerevisiae* (see Clark et al., *Nature* 287:504–509 (1980) and Stinchcomb et al., *J. Molec. Biol.* 158:157–179 (1982)). Episomes carrying the yeast CEN sequences display proper segregation into daughter yeast cells during mitosis and meiosis, in contrast to ARS plasmids lacking a centromere.

The best characterized centromeric DNAs originate from the budding yeast *Saccharomyces cerevisiae*. Clarke and Carbon, *Ann Rev Genet* 19:29–56 (1985). The DNA region required for centromere function in *S. cerevisiae* is approximately 120 bp long and is composed of three conserved domains: CDEI, an 8 bp element [(A/G)TCAC(A/G)TG], CDEII, an extremely [~90%] AT-rich region of approximately 80 bp, and CDEIII, a 25 bp element [TGTTT(A/T)TGNTTTCCGAAANN-NNAAA]. The molecular structure of centromeric DNAs from the fission yeast *Schizosaccharomyces pombe* have also been characterized. Several classes of *S. pombe* moderately repeated DNA elements have been identified which are found only in the centromere regions. These centromere-specific repetitive elements have been designated dg (3.8 kb), dh (4 kb), and yn by Yanagida and co-workers (Nakaseko et al., *Embo. J.* 5.:1011–1021 (1986); Nakaseko et al., *Nuc. Acid Res.* 15:4705–4715 (1987)), and K (6.4 kb), L (6 kb), and B (1 kb) by Carbon and his colleagues (Clarke et al., *PNAS* 83:8253–8257 (1986); Fishel et al., *Mol. Cell Biol.* 8:754–763 (1988)). The dg element has an AT-rich region and a 600 bp domain containing numerous small direct repeat motifs. Similarly, the dh element has an overall AT content approaching 70% and contains many short direct repeats. No nucleotide similarities to the *S. cerevisiae* CDEs have been found in the *S. pombe* elements.

Attempts to demonstrate that the *S. pombe* centromere-specific repetitive elements can function individually as centromeres have been unsuccessful. However, large restriction fragments (65 to 150 kb) carrying the entire fission yeast centromere regions of chromosome 1 or 3 function as centromeres when introduced into acentric episomes (Hahnenberger et al., *PNAS USA* 86:577–581 (1989)). These results indicate that either fission yeast centromeres are large composite structures that cannot be subdivided, or the functional fission yeast centromere element has not yet been identified.

In contrast to the detailed studies done in *S. cerevisiae* and *S. pombe*, essentially nothing is known about the molecular structure of functional centromeric DNA of higher eukaryotes. Ultrastructural studies indicate that higher eukaryotic kinetochores are large structures (e.g., mammalian kinetochore plates are approximately 0.3 µm in diameter) which possess multiple microtubule attachment sites (reviewed in Rieder, *Int. Rev. Cytol.* 79:1–58 (1982)). It is therefore likely that the centromeric DNA regions of these organisms will be corresponding large.

Telomeres, the last chromosomal element in lower eukaryotes to be cloned, are thought to be involved in the priming of DNA replication at the chromosome end (see, for example, Blackburn et al., *Ann. Rev. Biochem.* 53:163–194 (1984)). This is because conventional DNA polymerases are template dependent, synthesize DNA in the 5' to 3' direction, and require an oligonucleotide primer to donate a 3' OH group. When this primer is removed, unreplicated single-stranded gaps arise; most of these gaps can be filled in by priming from 3' OH groups donated by newly replicated strands located at the 5' end of the gap. However, the unreplicated gaps which lie next to the extreme 5' end of the DNA duplex cannot be primed in this manner. Consequently, telomeres must provide an alternative priming mechanism.

Telomeres are also responsible for the stability of chromosomal termini. Telomeres act as "caps," suppressing the recombinogenic properties of free, unmodified DNA ends (see Blackburn, supra). This reduces the formation of damaged and rearranged chromosomes which arise as a consequence of recombination-mediated chromosome fusion events.

Telomeres may also contribute to the establishment or maintenance of intranuclear chromatin organization through their association with the nuclear envelope (see, for example, Fussell, C. P., *Genetica* 62:192–201 (1984)).

Telomeric or telomeric-like DNA sequences have been cloned from several lower eukaryotic organisms, principally protozoans and yeast. The ends of the Tetrahymena linear DNA plasmid have been shown to function like a telomere on linear plasmids in *S. cerevisiae* (see Szostak, J. W., *Cold Spring Harbor Symp. Quant. Biol.* 47:1187–1194 (1983)). A telomere from the flagellate Trypanosoma has been cloned (see, for example, Blackburn et al., *Cell* 36:447–457 (1984). A yeast telomeric sequence has been identified (see, for example, Shampay et al., *Nature* 310:154–157 (1984)).

None of the essential components, including the telomeres, however, function in higher eukaryotic systems. For example, there have been numerous attempts to isolate ARSs from other eukaryotes by selecting for pieces of DNA that will serve as an ARS in yeast. While such DNA fragments can be readily identified, they do not promote extrachromosomal replication in cells from the donor organism.

DNA molecules carrying ARSs that function in yeast cells do not promote extrachromosomal replication of these molecules in mouse cells (see Roth et al., *Mol. Cell. Biol.* 3:1898-1908 (1983)). An ARS sequenced from cultivated tomato, which operates in yeast, fails to function in tomato cells (see Zabel, P., "Toward the Construction of Artificial Chromosomes for Tomato," In: *Molecular Form and Functions of the Plant Genome*, (Plenum Press (1985) and Jongsma et al., *Plant Molec. Biol.* 8:383-394 (1987)). Similarly, yeast CEN sequences do not function when introduced into mouse or Aspergillus chromosomes (Boylan, et al., *Mol. Cell. Biol.* 6:3621 (1986)). In addition, telomeres from the protozoan Tetrahymena do not function in cells of the vertebrate Xenopus (Yu, et al., *Gene* 56:313 (1987)). Finally, although researchers were able to show that a *S. pombe* chromosome can replicate at a reduced efficiency in mouse cells, the centromeres of this lower eukaryote apparently do not function in the higher eukaryote nucleus (see Allshire et al., *Cell* 50:391-403 (1987)).

Artificial chromosomes have been constructed in yeast using the three cloned essential chromosomal elements. Murray et al., *Nature* 305:189-193 (1983), disclose a cloning system based on the in vitro construction of linear DNA molecules that can be transformed into yeast, where they are maintained as artificial chromosomes. These artificial yeast chromosomes contain cloned genes, replicators, centromeres and telomeres but have an impaired centromeric function in short (less than 20 kb) artificial chromosomes.

The ability to construct artificial chromosomes that function in yeast, however, does not teach one skilled in the art how to construct an artificial chromosome using the essential elements which will function in higher eukaryotes. The cells of higher eukaryotic organisms differ from yeast cells in ways that place many further demands on the functioning of their genes. The amounts of DNA in higher eukaryotes is large, varying between species in ways that are not yet completely understood. They have more DNA and their genomes are composed of different classes of sequences: true gene regions interrupted by numerous and lengthy introns, structural sequences necessary for chromosome sorting during cell division, and various kinds of repetitive sequences.

Lower eukaryotic systems were the only source of the artificial chromosome essential elements until the teaching of the present invention. It is clear that the construction of an efficient, functional artificial plant chromosome requires the isolation of the three essential elements from plant chromosomes, and this novel methodology and the elements derived therefrom are taught by the present invention.

SUMMARY OF THE INVENTION

The present invention provides for the construction of a recombinant molecule which contains the telomere and, optionally, the centromere of a higher eukaryote.

The invention also provides for a method of producing a polypeptide which comprises cloning a gene sequence capable of producing the polypeptide into a recombinant molecule which contains a telomere and, optionally, the centromere of a higher eukaryote, introducing the recombinant molecule containing the cloned gene sequences into a recipient cell, and incubating the cell such that it produces the polypeptide.

This invention also discloses a novel method of isolating and enriching the telomeric clones of higher eukaryotic organisms by using genetic engineering methods in a suitable manner described hereinafter.

This invention also describes the structure of repetitive elements which contain telomere-similar sequences which lie in the centromere region of chromosome 1 of *A. thaliana*. Additionally, the structure of an unusual repetitive element which resides next to these telomere-similar repeats is described.

The invention also provides an alternate method for the transformation of plant cells by constructing functional artificial chromosome vectors.

Artificial chromosomes that function in higher eukaryotes have never been constructed. The present invention discloses for the first time the molecular cloning of telomeres and centromere sequences from *A. thaliana*, a small flowering plant in the mustard family. Before now, no essential chromosomal element had been isolated from a higher eukaryote. The cloned *A. thaliana* telomere and centromere serve as a starting point for the construction of a functional artificial plant chromosome.

Use of the artificial chromosome vector of the present invention solves many of the problems associated with the current transformation technology used to introduce new DNA into higher eukaryotic cells. Since artificial chromosomes are maintained in the cell nucleus as independently replicating DNA molecules, sequences introduced on such vectors are not subject to variable expression due to integration position effects.

The problem of DNA rearrangement which occurs when sequences are introduced by transfection protocols or using the Agrobacterium/T-DNA system can be avoided with the present invention. Integrative transformation systems generally involve introduction of DNA in recombinogenic form (e.g., DNA with free ends) and selection for transformants that splice together the incoming sequences and the host chromosome (see Orr-Weaver et al., *Proc. Natl. Acad. Sci. USA* 78:6354-6358 (1981)). Since an artificial chromosome can be delivered to the plant nucleus as an intact, unbroken, double-stranded DNA molecule with telomeric ends, DNA can be maintained stably in that form and rearrangements should not occur.

Artificial chromosome vectors can also be used to perform efficient gene replacement experiments. At present, gene replacement has not been demonstrated in a plant system and has only been detected at low frequency in mammalian tissue culture systems (see Thomas et al., *Cell* 44:419-428 (1986) and Smithies et al., *Nature* 317:230-234 (1985)). The reason for this is the high frequency of illegitimate nonhomologous recombination events relative to the frequency of homologous recombination events (the latter are responsible for gene replacement). Artificial chromosomes participate in homologous recombination preferentially. Since the artificial chromosomes remain intact upon delivery, no recombinogenic broken ends will be generated to serve as substrates for the extremely efficient illegitimate recombination machinery. Thus, the artificial chromosome vectors disclosed by the present invention will be stably maintained in the nucleus through meiosis and available to participate in homology-dependent meiotic recombination.

In addition, because in principle, artificial chromosomes of any length could be constructed using the teaching of the present invention, the vectors could be used to introduce extremely long stretches of foreign DNA into cells.

Another new and useful feature of the present artificial chromosome transformation system is the absence of host range limitations; foreign DNA can be delivered to plant cells directly without the use of Agrobacterium.

DESCRIPTION OF THE FIGURES

FIG. 2 shows a Southern blot representation of the hybridization of the pAtT4 insert to Bal31-treated *A. thaliana* nuclear DNA.

FIG. 3(A) depicts the chromosome configuration in a telotrisomic mutant. The extra telocentric chromosome has two telomeres: one identical to that present on the full length chromosomes, and a new telomere added adjacent to the centromere. A hypothetical restriction map shown under the linear chromosomal DNAs illustrates the expected correlation between the telotrisomic genotype and the presence of a novel telomeric restriction fragment.

FIG. 3(B) shows a Southern blot representation of three disomic and three telotrisomic plants from the progeny of a Tr5A telotrisomic parent probed with radiolabeled pAtT4 and washed at high stringency. A novel, polymorphic 15 kb DraI band, present in Tr5A DNA but absent from wildtype disomic (wt) DNA, is marked with an arrowhead.

FIG. 4 shows the DNA sequence of the pAtT4 insert. Insert sequences are shown in larger font and flanking vector sequences displayed in smaller font. The fusion of the blunt cloning site of the vector to the telomeric sequences occurs after the underlined sequence denoted ½ HincII. The MboI site of the insert, which is joined to the BamHI site of the vector, is underlined and labeled. The prevalent telomeric repeat 5'-[CCCTAAA]-3' is displayed in heptameric blocks. The two variant repeats, 5'-[CTCTAAA]-3', are underlined.

FIG. 5 shows a Southern blot representation of the pAtT4 insert hybridization to *Z. mays* DNA.

FIG. 6 shows a Southern blot representation of the pAtT4 hybridization to Bal31-treated human DNA.

FIG. 6(A) shows human genomic DNA [1 μg/ml] treated with Bal31 [1 U/ml] for 0 (lane 1), 5 (lane 2), 15 (lane 3), 30 (lane 4), and 60 minutes (lane 5), and subsequently digested with HindIII. The DNA was sized-fractionated by electrophoresis through a 0.7% agarose gel and transferred to a nylon membrane. The membrane was then probed with radiolabeled pAtT4 and washed at low stringency.

FIG. 6(B) shows the membrane in 5(A) rehybridized with a radiolabeled Xenopus rDNA clone (XI.4DNA), and washed at low stringency.

FIG. 7 schematically shows a procedure for making minichromosomes.

FIG. 8 schematically shows a shotgun cloning protocol for the functional selection of a plant ARS sequence.

FIG. 9 schematically shows a cloning protocol for cloning plant centromeres using telomeric probes and telotrisomic mutants.

FIG. 10 shows schemes for constructing plant artificial chromosomes utilizing *E. coli*/plant circular shuttle vectors (A); yeast/plant circular shuttle vectors (B); and yeast/plant linear shuttle vectors (C).

FIG. 13 shows the DNA sequence of repetitive elements from the telomere-similar region of pAtT12. The DNA sequences of three ~500 bp telomere-similar repetitive elements (pAtT20, pAtT24, and pAtT25) are aligned with the sequence of two interspersed ~180 bp elements (pAtT28 and pAtT29). Nucleotide identities to the consensus (plurality) are denoted by dots and differences are shown in the corresponding lines. Dashes denote deletions. The simple-sequence domain containing degenerate telomere motifs is located from nucleotides 150 to 350.

(Koornneef, "Genetic Maps" in Cold Spring Harbor Laboratory Press, Cold Spring Harbor, N.Y. (1987)) is shown at the left; map positions (in cM) of relevant genetic markers are given. The centromere region is magnified and correlated with the corresponding region of the RFLP map as described in the text. The centromere maps between tt-1 and ch-1 (denoted by the bracket), and is closely linked to the latter marker (indicated by the position of the circle). The range encompassing the two most likely map positions of the pAtT12 insert sequences relative to ch-1 and NIA2 (a nitrate reductase structural gene) is denoted by a bracket. The pAtT12 map position shown was determined using the codominant B and C RFLP alleles recognized by probe B since they were more informative than the dominant allele defined by probe A.

Figure 15:
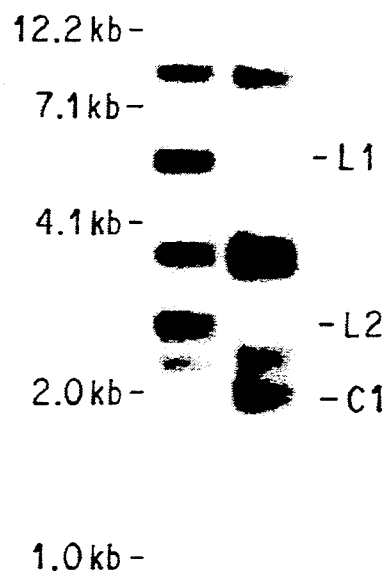

FIG. 15 shows that the flanking region of pAtT12 contains a moderately repetitive element. Total genomic DNA from the *A. thaliana* ecotypes Landsberg and Columbia were digested with DraI and size fractionated by electrophoresis through a 1% agarose gel. The DNAs were then transferred to a nylon membrane and hybridized with radiolabeled probe B (a 1 kb SacI fragment from the right-hand edge of the pAtT12 insert; the SacI site which lies directly adjacent to the BamHI site in the vector polylinker was used for convenience). The filters were washed in 0.2X SSC, 0.1X SSC@60° C. The polymorphic bands corresponding to the RFLP markers A, B, and C are shown.

Figure 16C:
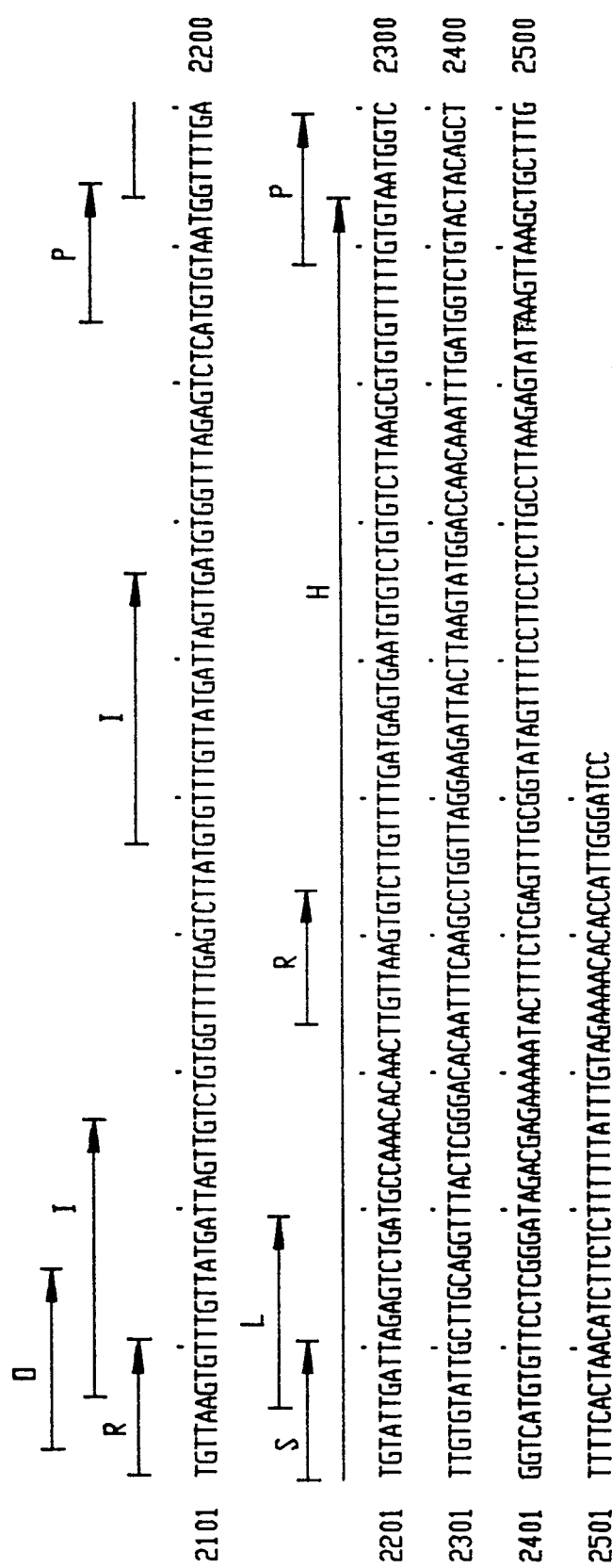

FIG. 16 shows the DNA sequence of the pAtT12 flanking region. The DNA sequence of the 2553 bp HindIII-BamHI fragment corresponding to the flanking region is shown. The locations of the direct repeats are indicated by the lettered arrows over the sequence. The individual members of the largest direct repeats, A and H, share 94% and 92% nucleotide identity, respectively, with their cognate. The remaining repeats are identical to their cognate(s), with the exception of B and C which contain 1 bp mismatches. Most motifs are repeated twice, except L (3X) and S (5X). The boundary between the telomere-similar repeat domain and the flanking region occurs around nucleotide 90, since nucleotides 1-89 share significant similarity with the telomere-similar repetitive elements. The SacI site which defines the left-hand boundary of probe B begins at nucleotide 1582.

DESCRIPTION OF THE PREFERRED EMBODIMENTS

I. Definitions and Background

In the following description, reference will be made to various methodologies well known to those of skill in the art of recombinant genetics. Publications and other materials setting forth such well known methodologies will be referred to in the course of this description, and are incorporated herein by reference.

The present invention relates to the construction of artificial chromosome vectors for the genetic transformation of plant cells, processes for their preparation, uses of the vectors, and systems transformed by them. Standard reference works setting forth the general principles of recombinant DNA technology include Lewin, B. M., *Genes II,* John Wiley & Sons, Publishers, N.Y. (1985). Other works describe methods and products of genetic engineering; see, e.g., Maniatis et al., *Molecular Cloning, A Laboratory Manual* (Cold Spring Harbor Laboratory, 1982); Watson et al., *Recombinant DNA: A Short Course* (W. H. Freeman and Co., 1983); Setlow et al., *Genetic Engineering: Principles and Methods* (Plenum Press, 1979); and Dillon et al., *Recombinant DNA Methodology* (John Wiley & Sons, 1985).

By "transformation" or "transfection" is meant the acquisition in cells of new genetic markers through incorporation of added DNA. This is the process by which naked DNA is introduced into a cell, resulting in a heritable change.

As used herein, "eukaryote" refers to living organisms whose cells contain nuclei. A eukaryote may be distinguished from a "prokaryote" which is an organism which lacks nuclei. Prokaryotes and eukaryotes differ fundamentally in the way their genetic information is organized, as well as their patterns of RNA and protein synthesis.

By the term "lower eukaryote" is meant a eukaryote characterized by a comparatively simple physiology and composition, and unicellularity. Examples of lower eukaryotes include flagellates, ciliates, and yeast, for example.

By contrast, the term "higher eukaryote" means a multicellular eukaryote, characterized by its greater complex physiological mechanisms as well as its ability to interact with its environment in a more sophisticated manner. Generally, more complex organisms such as plants and animals are included in this category. Preferred higher eukaryotes to be transformed by the present invention include, for example, monocot and dicot angiosperm species, gymnosperm species, fern species, plant tissue culture cells of these species, and algal cells. It will of course be understood that prokaryotes and eukaryotes alike may be transformed by the methods of this invention.

As used herein, the term "plant" includes plant cells, plant protoplasts, plant calli, and plant cells or tissue culture from which whole plants can be regenerated.

A variety of processes are known which may be utilized to effect transformation; i.e., the inserting of a heterologous gene into a host cell, whereby the host becomes capable of efficient expression of the inserted genes. By "gene" is meant a DNA sequence that contains information for construction of a polypeptide or protein, and includes 5' and 3' ends.

As used herein, "heterologous gene" is a structural gene that is foreign, i.e., originating from a donor different from the host or a chemically synthesized gene, and can include a donor of a different species from the host. The heterologous gene codes for a polypeptide ordinarily not produced by the organism susceptible to transformation by the expression vehicle. Another type of "heterologous gene" is an altered gene from the host itself. One example of such an altered gene useful in the present invention is a mutant gene which encodes a herbicide-resistant form of a normally occurring enzyme.

By "host" is meant any organism that is the recipient of a replicable plasmid, or expression vector. Ideally, host strains used for cloning experiments should be free of any restriction enzyme activity that might degrade foreign DNA. For example, it is advantageous that a preferred *E. coli* host strain be defective in homology-based recombination (recA) since inadvertent recombinational events may threaten the integrity of the cloned DNA. The nucleic acid of the host should also be easily separable from that of the cloning vector by physical means (e.g., differential centrifugation based on G-C content or encapsulation) or differ in its reactivity to alkali or organic acids (phenol). Preferred examples of host cells for cloning, useful in the present invention, are bacteria such as *Escherichia coli, Bacillus subtilis, Pseudomonas, Streptomyces, Salmonella,* and yeast such as *S. cerevisiae.*

By "expression" is meant the process by which a structural gene produces a polypeptide. It involves transcription of the gene into messenger RNA (mRNA) and the translation of such mRNA into polypeptide(s).

A method useful for the molecular cloning of DNA sequences includes in vitro joining of DNA segments, fragmented from a source high molecular weight oligonucleotide, to vector DNA molecules capable of independent replication. The cloning vector may include plasmid DNA (see Cohen, et al., *Proc. Natl. Acad. Sci. USA* 70:3240 (1973)), phage DNA (see Thomas, et al., *Proc. Natl. Acad. Sci. USA* 71:4579 (1974)), or SV40 DNA (see Nussbaum, et al., *Proc. Natl. Acad. Sci.* USA 73:1068 (1976)).

The term "plasmid" or "cloning vector" as used herein refers to a closed covalently circular extrachromosomal DNA which is able to autonomously replicate in a host cell and which is normally nonessential to the survival of the cell. A wide variety of plasmids are known and commonly used in the art (see, for example, Cohen, S. et al., U.S. Pat. No. 4,468,464, which discloses examples of DNA plasmids). In a preferred embodiment, the plasmids used in the present invention are identical except for the orientation of the polylinker (see Levinson, et al. *J. Mol. Appl. Genet.* 2:507–517 (1984)). In a preferred embodiment, the plasmids used in the present invention also contain an M13 origin which allows single-stranded versions of the plasmids to be generated.

The single-stranded, filamentous bacteriophage M13 is a wellknown cloning vector (see, for example, Messing, et al., *Proc. Natl. Acad. Sci. USA* 74:3642–3646 (1977); Van Wegenbeek et al., *Gene* 11:129–148 (1980); and Gillam et al., *Gene* 12:129–137 (1980)). Preferably, the small plasmids pSDC12 and pSDC13, with cloning polylinker, may be used.

By "polylinker" it is meant a DNA molecule, generally 50 to 60 nucleotides long and synthesized chemically. In a preferred embodiment, this fragment contains one, or preferably more than one, restriction enzyme site for a blunt-cutting enzyme and a staggered-cutting enzyme, preferably BamHI. One end of the polylinker fragment is adapted to be ligatable to one end of the linear molecule and the other end is adapted to be ligatable to the other end of the linear molecule.

A fragment of DNA, from any source whatsoever, may be purified and inserted into the plasmid at any of the polylinker region restriction endonuclease cleavage sites. DNA to be inserted into a plasmid may be from prokaryotes, such as *Escherichia coli, Bacillus subtilis, Streptomyces lividans* or the like; from viruses which infect prokaryotes, such as lambda, T4, C31 or the like; from eukaryotes, such as *Saccharomyces cerevisiae, Mus musculus, Homo sapiens,* or the like; or from viruses which infect eukaryotes such as Herpes Simplex, SV40, or the like.

The techniques and procedures required to accomplish insertion are well-known to the art (see Maniatis et al., *Molecular Cloning, A Laboratory Manual,* Cold Spring Harbor Laboratory, 1982). Typically, this is accomplished by incubating the plasmid in the presence of a restriction endonuclease such that the restriction endonuclease cleaves the plasmid to produce a linear molecule.

Endonucleases preferentially break the internal phosphodiester bonds of polynucleotide chains. They may be relatively unspecific, cutting polynucleotide bonds regardless of the surrounding nucleotide sequence. However, the endonucleases which cleave only a specific nucleotide sequence are called restriction enzymes. Restriction endonucleases generally internally cleave foreign DNA molecules at specific recognition sites, making breaks within "recognition" sequences that exhibit two-fold symmetry around a given point. Because the same sequence (running in opposite directions) is found on both strands, such enzymes always create double-stranded breaks.

Most often, the enzymes make a staggered cleavage, yielding DNA fragments with protruding single-stranded 5' termini. Such ends are said to be "sticky" or "cohesive" because they will hydrogen bond to complementary 3' ends. As a result, the end of any DNA fragment produced by an enzyme, such as EcoRI, can anneal with any other fragment produced by that enzyme. This properly allows splicing of foreign genes into plasmids, for example. For purposes of the present invention, preferred restriction endonucleases include HincII, MboI, and BamHI.

Some of these endonucleases create fragments that have blunt ends, that is, that lack any protruding single strands. When DNA has been cleaved with restriction enzymes that cut across both strands at the same position, blunt end ligation can also be used to join the fragments directly together.

The great advantage of this technique is that any pair of ends may be joined together, irrespective of sequence.

Those nucleases that preferentially break off terminal nucleotides are referred to exonucleases. For example, small deletions can be produced in a circular DNA molecule by cleaving it with a restriction enzyme that linearizes it. The linear molecules are then treated with an exonuclease which starts from each 3' end of the DNA and chews away single strands in a 3' to 5' direction, creating a population of DNA molecules with single-stranded fragments at each end, some containing terminal nucleotides. The nuclease Bal31 has often been used because this enzyme chews away both strands from the ends of linear DNA molecules. Exonucleases to be used in the present invention preferably include Bal31, SI, or ExoIII.

Once the source DNA sequences have been cleaved and the plasmid linearized, they are incubated together and enzymes capable of mediating the ligation of the two DNA molecules are added. Preferred enzymes include T4 ligase, *E. coli* ligase, or other similar enzymes. The action of these enzymes results in the sealing of the linear DNA to produce a closed covalently circular DNA molecule containing the desired fragment (see, for example, U.S. Pat. Nos. 4,237,224; 4,264,731; 4,273,875; 4,322,499 and 4,336,336). These nucleolytic reactions can be controlled by varying the time of incubation, the temperature, and the enzyme concentration needed to make deletions.

It is to be understood that the termini of the linearized plasmid and the termini of the DNA fragment being inserted must be complementary in order for the ligation reaction to be successful. Suitable complementarity can be achieved by choosing appropriate restriction endonucleases (i.e., if the fragment is produced by the same restriction endonuclease as that used to linearize the plasmid, then the termini of both molecules will be complementary). As discussed previously, in a preferred embodiment, at least two classes of the plasmids used in the present invention are adapted to receive the foreign oligonucleotide fragments in only one orientation.

After joining the DNA segment to the plasmid, the resulting hybrid DNA (known as a chimera) can then be selected from among the large population of clones or libraries.

As used herein, a "library" is a pool of random DNA fragments which are cloned. In principle, any gene can be isolated by screening the library with a specific hybridization probe (see, for example, Young et al., In: *Eukaryotic Genetic Systems, ICN-UCLA Symposia on Molecular and Cellular Biology, VII* (New York, Academic Press), pp. 315-331 (1977)). Each gene library may contain the DNA of a given organism inserted as discrete restriction enzyme-generated fragments into many thousands of plasmid vectors. For purposes of the present invention, *E. coli*, yeast, and Salmonella plasmids are particularly useful when the genome inserts come from other organisms.

The feasibility of constructing and screening libraries from the DNA of organisms with small genomes, such as Drosphila or yeast, has been demonstrated (see, for example, Weinsink et al., *Cell* 3:315-325 (1974)) and Carbon et al., In: *Recombinant Molecules: Impact on Science and Society* (Raven Press), pp. 335-378 (1977)). Handling libraries from larger genomes, however, is difficult because of the numerous technical limitations inherent in manipulating such a complex system.

By "hybridization" is meant the pairing of complementary RNA and DNA strands to produce an RNA-DNA hybrid, or the partial pairing of DNA single strands from genetically different sources.

As used herein, a "probe" is any biochemical (usually tagged in some way for ease of identification), used to identify or isolate a gene, a gene product, or a protein.

A "selectable marker" is a gene with a known location on a chromosome and a clear-cut phenotype, permitting the identification of the existence of a particular sequence in which the marker has been attached. Use of selectable markers is described, for example, in Broach et al., *Gene* 8:121-133 (1979). Examples of selectable markers include the thymidine kinase gene, the cellular adenine-phosphoribosyltransferase gene and the dihydrylfolate reductase gene, and preferably hygromycin phosphotransferase genes and neomycin phosphotransferase genes, among others. Preferred selectable markers in the present invention include genes whose expression confer an antibiotic resistance to the host cell, sufficient to enable the maintenance of a plasmid within the host cell, and which facilitate the manipulation of the plasmid into new host cells. Of particular interest in the present invention are proteins conferring cellular resistance to ampicillin, chloramphenicol, tetracycline, and G-418, for example.

II. Telomere

Based upon nuclease cleavage and ligation methods, utilization of plasmids with polylinkers oriented in opposite orientation, and the use of an M13 helper phage, the telomeres of higher eukaryotes, preferably of a plant, may be isolated.

In a preferred embodiment, unrestricted, high molecular weight nuclear DNA from any source whatsoever may be treated briefly with an exonuclease to create blunt ends. (Source DNA may be from prokaryotes, eukaryotes, or viruses which infect prokaryotes or eukaryotes, as previously detailed.) The blunt ends of the fragmented DNA are then ligated to a small *E. coli* plasmid cloning vector, for example, which has previously digested with two different restriction endonucleases to generate one blunt end and one sticky end. The ligation products are then digested with the restriction endonucleases, leaving compatible ends. Next, the restriction fragments are ligated to form circles which are then propagated in an *E. coli* host, for example.

Two independent primary libraries are constructed in this fashion; one using pSDC12, for example, and the other using the complementary vector, pSDC13.

The primary libraries will contain inserts corresponding to sequences that lie adjacent to the ends of the large genomic DNA fragments. Since chromosome size DNA cannot be isolated, only a small fraction of the inserts are derived from telomeric ends; the remainder will represent sequences that lie next to random, shear-generated ends. Thus, the ratio of telomeric to random inserts is a function of chromosome size and the average size of the isolated genomic DNA fragments. According to the present invention, the *A. thaliana* telomeric clone can be obtained at a frequency of $10^{-3}$ in each of the primary libraries. Each library should be composed of about 5000 members in order to ensure that each primary library has at least one telomeric clone.

To increase the representation of telomeric clones, plasmids containing inserts that are present in both primary libraries must be identified and saved, and random clones, isolated from broken ends, discarded, to form a new collection of clones referred to as the secondary library. This procedure will save telomeric clones in which the primary libraries were large enough to ensure that each contained at least one telomeric clone.

Although methods for the enrichment of desired DNA sequences prior to cloning are known (see, for example, Tilghman et al., *Proc. Nat'l Acad Sci.* USA 74:4406-4410 (1977)), the novel enrichment protocol of the present invention capitalizes on the underrepresentation of nontelomeric sequences in the two primary libraries. Random, nontelomeric single copy sequences will not be represented in both primary libraries due to the small insert size (average=0.3 kb) and the small member size (about 5,000/primary library) of the primary libraries. Each primary library can represent, at most, only 15,000 kb (5,000×0.3 kb) of a 70,000 kb haploid genome. Because the probability of cloning any particular DNA sequence independently from random chromosomal ends in both primary libraries is quite low, nontelomeric sequences will be underrepresented and enrichment for telomeric clones can thus be achieved by saving clones with inserts common to both primary libraries (see Table 1).

To assemble a secondary library, single-stranded DNA plasmids are first made by infection of both primary libraries with an M13 helper phage, for example. By utilizing plasmids with polylinkers oriented in opposite directions, infection with the M13 bacteriophage can separate the double-stranded DNA into two sets of complementary single-stranded molecules (see, for example, Levinson, et al., *J. Mol. Appl. Genet.* 2:507-517 (1984)). The single-stranded DNAs are mixed and allowed to anneal. Since the M13 system packages only one strand of the plasmid, the vector sequences can not hybridize to themselves. A plasmid can only cross-hybridize to another single-stranded plasmid if the inserts of these plasmids are homologous and represent complementary strands.

The reassociation of two complementary sequences of DNA occurs by base pairing. Renaturation of DNA depends on random collision of the complementary strains; it therefore follows second order kinetics. This means that the rate of reaction is governed by the concentration of DNA that is single-stranded at any particular time, and the time of incubation. In a preferred embodiment, the concentration of such single-stranded plasmids will be 400 μg/ml.

The single-stranded plasmids with complementary DNA inserts cross-hybridize to form a double-stranded DNA section and the single-stranded plasmids without such cross-hybridizing inserts remain as single-stranded DNA molecules. Hydroxylapatite chromatography, which distinguishes between single- and double-stranded DNAs, can be used to purify cross-hybridizing single-stranded plasmids (see, for example, Britten, et al., *Methods Enzymol.* 29:363 (1974)). After isolation, the cross-hybridizing plasmids may be transformed into a recombination-deficient *E. coli* host, for example.

The secondary library is thereafter screened in order to identify the clones that contain the specific hybrid DNA, or telomeric insert, desired. The screening of restriction fragments may be accomplished by a variety of methods; for example, gel electrophoresis, Southern blotting, buoyant density, etc. In a preferred embodiment, this screening for telomeric sequences may be correlated to exonuclease sensitivity. Telomeric DNA sequences are preferentially sensitive to exonuclease attack since they always reside next to a DNA end. (See, for example, Yao, et al., *Proc. Natl. Acad. Sci. USA* 78:7436-7439 (1981)). Nontelomeric sequences are degraded by exonuclease treatment of high molecular weight genomic DNA only when an infrequent random breakage occurs nearby.

In a preferred embodiment, the screen may be conducted using Southern blots (see Southern, *J. Mol. Biol.* 98:503 (1975)) prepared as follows. Source nuclear DNA can be digested with an exonuclease for various lengths of time (see FIG. 2) and subsequently digested with a restriction endonuclease, size-fractionated by agarose gel electrophoresis and transferred to nylon membranes. These Southern blots may then be probed with plasmid DNAs (pooled five at a time) prepared from clones in the secondary library. Plasmids which hybridize to restriction fragments which shift electrophoretic mobility upon increasing exonucleolytic digestion are telomeric clones.

Using this cloning and enrichment method, a telomeric clone which hybridized to exonuclease-sensitive restriction fragments was isolated from *A. thaliana*. This plasmid, designated pAtT4, was discovered to be described by the DNA sequence 5'-[CCCTAAA]-3' (see Example 5). A variant repeat was also found consisting of tandemly repeated blocks of the base sequence 5'-[CTCTAAA]-3'. The pAtT4 plasmid was deposited under the terms of the Budapest Treaty at the American Type Culture Collection, Rockville, Md., before the filing date of this application, and assigned Accession Number ATCC 67577. It is described more fully in FIG. 4.

III. Autonomous Replicating Sequence

Prior attempts to isolate functional higher eukaryotic replication origins have been largely unsuccessful. Some have attempted to isolate these ARSs by selecting for ARS function in yeast (see, for example, Ross et al., *Mol. Cell. Biol.* 3:1898-1908 (1983); Stinchcomb et al., *Proc. Natl. Acad. Sci. USA* 77:4559-4563 (1980)). Unfortunately, these "ARS" sequences do not function to support extrachromosomal replication when introduced back into the natural host organism (see Jongsma et al., *Plant Mol. Biol.* 8:383-394 (1987)). The inventors have discovered that the best approach for isolating plant replication origins relies on functional tests for extrachromosomal replication in plant cells.

The present invention discloses a novel method for isolating the ARS sequences which involves the formation of minichromosome derivatives of natural chromosomes (see FIG. 7). It has been demonstrated in yeast that inverted repeats of telomeric sequences are "resolved" by an unknown mechanism which results in a double-stranded cleavage between the inverted repeats (see, for example, Szostak, *Cold Spring Harbor Symp. Quant. Biol.* 47:1187-1193 (1983)). After an inverted telomere repeat is introduced into a chromosome, a resolution reaction will lead to scission of the chromosome and formation of two chromosomal fragments, each with two telomeres (see Murray et al., *Cell* 45:529-536 (1986)). This process generates a minichromosome small enough to be isolated intact ($\leq 1$ Mb) allowing further manipulation by in vitro techniques to delimit the sequences responsible for autonomous replication. Example 11 details illustrative experimental procedures to be followed.

A second novel method disclosed by the present invention for isolating functional plant origins is a shotgun cloning approach (see FIG. 8). Higher eukaryotic organisms have many replication origins distributed throughout their genomes. The *A. thaliana* genome contains approximately 1000 origins spaced every 70 kb along the chromosome (see Van't Hof et al., *Chromosoma* 68:269-285 (1978)). Therefore, it is quite reasonable to look for random fragments of genomic DNA from *A. thaliana* which promote extrachromosomal replication. The details of performing such a shotgun cloning strategy are presented in Example 12.

IV. Centromere

As previously discussed, a centromere is the primary constriction of the chromosome and the site of kinetochore assembly (see Blackburn et al., *Ann. Rev. Biochem.* 53:163-194 (1984); Clarke et al., *Ann. Rev. Genet.* 19:29-56 (1985)). The kinetochore is the physical structure that mediates the attachment of the spindle fibers to the chromosome and is therefore responsible for the proper partitioning of the chromosomes at mitosis and meiosis. The DNA sequences found at the centromere (CEN sequences) presumably play a role in specifying kinetochore assembly.

CEN sequences have been isolated from *S. cerevisiae* and *Schizosaccharomyces pombe*. The functional CEN sequences of *S. cerevisiae* are less than 200 bp long and consist of three conserved sequence elements (see Clarke, supra). The functional CEN sequences in *S. pombe* have not yet been defined precisely (see Nakaseko et al., *EMBO J.* 5:1011-1021 (1986); Chikashige et al., *Cell* 57:739-751 (1989)).

CEN sequences from a higher eukaryotic system have not been isolated. In contrast to *S. cerevisiae* yeast kinetochores, which cannot be seen under the microscope, kinetochores from higher eukaryotes are extremely large (up to 0.7 microns), indicating that higher eukaryotic CEN sequences constitute long stretches of DNA (see, e.g., Bloom et al., *Cell* 29:305-317 (1982); Ris et al., *Chromosoma* 82:153-170 (1981); Sakai-Weda, A., *Cytologia* 48:253-258 (1983)).

The cloning strategy for isolation of plant CEN sequences used in the present invention capitalizes on the availability of cloned telomeric sequences and telotrisomic mutants of *A. thaliana* that possess a telomere in a new chromosomal location (see FIG. 9).

Telotrisomics are a special type of trisomic mutant that contain an extra chromosome arm in the form of a telocentric chromosome. Koornneef et al., *Genetica* 61:41-46 (1983) isolated Tr5A, the telotrisomic mutant used here, as a derivative of a primary trisomic line which contained an extra intact chromosome number 5. Telotrisomics arise from primary trisomic lines as a result of breakage of the extra chromosome when it exists as an unpaired univalent during meiosis; the breakage is thought to occur at, or close to, the centromere. The telocentric is formed by a "healing" event which leads to addition of a new telomere at the site of breakage.

A telotrisomic mutant has two extra telomeres in each nucleus: 1) the telomere on the distal tip of the extra chromosome arm which is identical to the telomere on the corresponding full length chromosome and 2) a new telomere adjacent to the centromere which has no counterpart in the normal chromosome complement.

The new telomere in the telotrisomic mutant Tr5A may be detected as a restriction fragment length polymorphism (RFLP) on Southern blots comparing telotrisomic genomic DNA and wild type disomic genomic DNA which have been probed with the cloned *A. thaliana* telomere (see Example 7).

In a preferred embodiment, once a telotrisomic RFLP has been identified, a genomic library may be constructed to clone the restriction fragment representing the CEN-telomere fusion (see Example 8).

Several tests can be used to determine if the clones isolated by this procedure represent *A. thaliana* CEN sequences. First, the putative CEN sequences are used as hybridization probes on Southern blots of all known telotrisomic mutants. If the probe represents authentic CEN sequences, it recognizes different RFLPs in each telotrisomic mutant, corresponding to the different CEN-telomere fusion events.

Functional assays for CEN sequences may also be used. The development of acentric autonomously replicating plant vectors, previously discussed, effectuates assays of potential CEN sequences for partitioning function. The acentric vectors are lost at a high frequency in the absence of selection due to the nondisjunction of replicating molecules. Addition of a functional centromere causes proper partitioning of the replicated molecules to daughter cells, leading to stable maintenance of the extrachromosomal vectors (see Hsiao et al., *Proc. Natl. Acad. Sci. USA* 78:3760-3764 (1981)).

Another functional test for CEN activity which may be used in the present invention is the creation of dicentric chromosomes (see Mann et al., *Proc. Natl. Acad. Sci. USA* 80:228-232 (1983)). Dicentric chromosomes are broken during anaphase when the two centromere/kinetochores become attached via spindle fibers to opposite poles. The breakage often leads to loss or rearrangement of the effected chromosome. To perform a dicentric assay, putative CEN sequences can be integrated into plant chromosomes using the Agrobacterium/T-DNA system. The introduced sequences which function as a centromere cause a dicentric chromosome to be created. This chromosome undergoes breakage, followed by rearrangement or chromosome loss; these events can be detected by karyotype analysis (i.e., microscopic examination of the chromosomes) and/or the loss of marker genes introduced along with the CEN sequences.

A different experimental approach to assaying putative CEN sequences involves characterization of proteins which bind to these sequences. Such proteins can be purified by affinity chromatography using the putative CEN sequences as a binding substrate (see Kadonaga et al., *Proc. Natl. Acad. Sci. USA* 83:5889-5893 (1986)). Antibodies raised against the proteins are then used to localize the antigen on the chromosome using in situ techniques. Authentic CEN binding proteins are thus localized at the centromere.

The most preferred methods for isolating the genome clones containing two classes of repetitive DNA elements derived from the centromere region of chromosome 1 of *A. thaliana* are described in Examples 10-14.

V. Construction of Chromosomes

Having now disclosed novel recombinant molecules and methods for preparing them so as to obtain functional essential chromosomal elements, it will be possible for those of ordinary skill in the art to construct such artificial chromosomes. Useful construction methods are well-known (see, for example, Maniatis, T., et al., *Molecular Cloning: A Laboratory Manual* (Cold Spring Harbor, 1982)). In addition to the essential elements, a selectable plant marker (e.g., antibiotic resistance gene), and a cloning site for insertion of foreign DNA must be included. In order to propagate the vectors in *E. coli*, it is necessary to convert the linear molecule into a circle by addition of a stuffer fragment between the telomeres, as indicated in FIG. 8. An *E. coli* plasmid replication origin and selectable marker must also be included.

Artificial plant chromosomes which replicate in yeast may also be constructed to take advantage of the large insert capacity and stability of repetitive DNA inserts afforded by this system (see Burke et al., *Science* 236:806-812 (1987)). In this case, yeast ARS and CEN sequences are added to the vector. The artificial chromosome is maintained in yeast as a circular molecule using the stuffer fragment to separate the telomeres.

VI. Plant Cell Transformation

Deproteinized DNA may be introduced into plant cells by the following several methods known in the art. For example, Shillito et al., *Biotechnology* 3:1099-1103 (1985) detail a protocol for the stable transformation of plant protoplasts at frequencies of up to 2% using electroporation.

Other methodologies are also useful in the present invention. Microinjection techniques are disclosed in Crossway et al., *Mol. Gen. Genet.* 202:179-185 (1986). Microprojectile delivery may also be used (see Klein et al., *Nature* 327:70-73 (1987)).

EXAMPLES

Having now fully described the present invention, the same will be more clearly understood by reference to certain specific examples which are included herewith for purposes of illustration only, and not intended to be limiting of the invention, unless specified.

The following experimental parameters were utilized in all manipulations.

Plasmids and Probes

Poly d(CA/GT) was purchased from Boehringer Mannheim Biochemicals. pSDC12 and pSDC13 are described in Levinson et al., *J. Mol. Appl. Genet.* 2:507-517 (1984). pKDR1 and pKDR2 contain the soybean rRNA genes on 3.75 and 3.9 kb EcoRI fragments respectively (Echenrode et al., *J. Mol. Evol.* 21:259-269 (1985)). pUC12 is described in Viera et al., *Gene* 19:259-268 (1982). M13mp18 is described in Yanisch-Perron et al., *Gene* 33:103-119 (1985). pbluescript KS was obtained from Stratagene. pARR16 and pARR12 contain 2.5 kb and 180bp *A. thaliana* EcoRI fragments consisting of rDNA and rDNA spacer DNA cloned in pUC12 respectively; pARR20-1 contains a 180bp HindIII fragment corresponding to the 180bp tandem repeat family described by Martinez-Zapater et al., *Mol. Gen. Genet.* 204:417-423 (1986), cloned in pUC12; and X1.4DNA is a Xenopus rDNA clone (Maden et al., *Nucl. Acid Res.* 6:817-830 (1979)). All DNA was prepared by standard procedures (Ausubel et al., *Current Protocols in Molecular Biology* (New York: John Wiley & Sons) (1987)). *A. thaliana* telomeric probes were generated by radiolabeling the 0.4 kb PstI-BamHI insert of pAtT4 (described herein and in Richards et al., *Cell* 53:127-136 (1988)). Radiolabeled probes were prepared either by nick translation or the random priming method using kits purchased from Boehringer Mannheim Biochemicals.

Preparation of Genomic DNAs

*A. thaliana* nuclear DNA (average size of approximately 100 kb) was prepared as described by Hamilton et al., *Ann. Biochem.* 49:48 (1972). Genomic DNA from the *A. thaliana* Landsberg telotrisomic mutant Tr5A and its disomic siblings (Koornneef et al., *Genetica* 61:41 (1983)) was prepared by the miniprep procedure of Dellaporta et al., *Plant Mol. Biol. Rptr.* 1:19-21 (1983). Genomic DNA preparation from all other plant species was performed as described in Ausubel et al., supra (1987). Human DNA was prepared by lysis of monolayers of HeLa cells with 100 mM Tris-HCl pH 8.0, 50 mM EDTA, 500 mM NaCl, 1% SDS, and 100 µg/ml Proteinase K. After incubation at 50° C. for 1 hour the lysates were phenol-extracted twice and chloroform-extracted once. The genomic DNA was then collected by ethanol precipitation.

Source of Enzymes

All restriction enzymes were purchased from New England Biolabs, Boehringer Mannhein Biochmeical, or International Biotechnologies, Inc. Bal31 and T4 DNA Ligase were purchased from New England Biolabs or United States Biochemicals.

Southern Hybridizations

Total genomic DNA from the Landsberg and Columbia ecotypes were prepared as described in Ausubel et al., *Current Protocols in Molecular Biology*: (New York: John Wiley & Sons) (1987). *A. thaliana* nuclear DNA was prepared by the protocol outlined in Olszewski et al., *Nuc. Acids Res.* 16:10765-10782 (1988).

Exonuclease digestion of *A. thaliana* nuclear DNA was performed using 0.25 U/ml of Bal31 nuclease at 30° C. at a DNA concentration of 10 µg/ml in 12 mM $CaCl_2$, 24 mM $MgCl_2$, 0.2 M NaCl, 20 mM Tris-HCl (pH 8.0), 1 mM EDTA, 100 µg/ml BSA.

Southern blots were prepared using nylon membranes (GeneScreen, NEN) and the UV cross-linking protocol of Church et al., *PNAS USA* 81:1991-1995 (1984). Hybridization were carried out in 0.5 M Na-$HOP_4$ (pH7.2), 7% SDS, 1 mM EDTA, 1% BSA (Church et al., supra). Hybridization temperatures and wash conditions are noted in the appropriate figure legends.

DNA Sequencing

The ~500 bp and ~180 bp HindIII fragments were prepared for sequencing by subcloning into either pUC12 or mp18 using standard procedures (Ausubel et al., supra (1097)). The following subclones were sequenced: pAtT20 (527 bp), pAtT24 (491 bp), pAtT25 (483 bp), pAtT28 (183 bp), and pAtT29 (183 bp).

The pAtT12 flanking region was subcloned into pBluescript KS - to generate pAtT27. Deletion derivatives of pAtT27 suitable for sequencing were made using the nested exoIII/nuclease S1 deletion procedure (Ausubel et al., supra (1987)).

Dideoxy sequencing reactions were carried out, on both single-stranded and double-stranded templates, using Sequenase enzyme and kits purchased from United States Biochemicals. Many regions were sequenced using oligonucleotide primers made on a Biosearch DNA synthesizer (New Brunswick Scientific).

RFLP Mapping

The RFLP mapping was done as described in Cheng et al., *EMBO J.* 7:3309-3314 (1988) and Nam et al., *The Plant Cell* 1:699-705 (1989). Briefly, inner ecotype crosses between wild type Columbia and various Landsberg marker lines (carrying multiple homozygous recessive mutations) were conducted. Genomic DNA was prepared from individual phenotyped F2 plants (represented by pooled F3 progeny) and Southern blots of these DNAs were prepared. The blots were then hybridized with the collection of cosmid clones and particular clones of interest. The resulting hybridization patterns were analyzed and segregating RFLP alleles noted. The likely orders and map positions of the RFLPs were determined using the MAPMARKER program (Lander and Green, *PNAS USA* 84:2363-2367 (1987); Lander et al., *Genomics* 1:174-181 (1987)).

EXAMPLE 1

Construction of Primary Library

High molecular weight genomic DNA was prepared and treated with Bal31 exonuclease to remove approximately 10 bps from every double-stranded end. The exonuclease digestion ensured that Bal31-susceptible terminal structures at the telomere (such as a hairpin) would be removed and that a blunt end suitable for ligation would be created.

The Bal31-treated blunt ends of the genomic DNA were ligated independently to the plasmid cloning vectors pSCD12 and pSDC13 that had earlier been digested with BamHI and HincII (which cleave in the polylinker, leaving one blunt HincII end and one sticky BamHI end) to generate linear vector DNAs with non-compatible ends. The ligation products were then digested with BamHI and MboI to generate linear chimeric DNAs with compatible ends (MboI, which recognizes the sequence 5'-GATC-3', cleaves genomic DNA frequently (about every 300 bp) leaving BamHI compatible ends; MboI does not cleave within the vector sequences because pSDC12 and pSDC13 were purified from a dam+ host). The linear chimeric DNAs were circularized by ligation at low DBA concentration and transformed into an F+ recA E. coli host (JM109) to form one pSCD12 and one pSDC13 primary library.

Specifically, 2 μg of genomic DNA were digested for 0.5 min (A. thaliana) or 2 min (S. cerevisiae) with 0.25 U/ml Bal31 nuclease at a DNA concentration of 10 μg/ml at 30° C. as described below. It was previously determined that under these conditions the rate of Bal31 exonucleolytic digestion was approximately 15 bp/min/end. pSDC12 and pSDC13 were digested separately with HincII followed by digestion with BamHI; the DNAs were precipitated with spermine and the 5' phosphates were removed with calf intestinal phosphatase. (The phosphatase step was omitted when constructing the yeast primary libraries, resulting in a high number of plasmids without inserts.) The linearized plasmid DNAs were ligated to the Bal31-treated yeast or A thaliana genomic DNAs with T4 DNA Ligase at 16° C. using 20,000 U/ml of enzyme, a 10 fold molar excess of vector to genomic DNAs, and a DNA concentration of 130 μg/ml. The ligation products were digested with MboI and BamHI and circularized with T4 DNA Ligase at 4° C. using 80 U/ml of enzyme at a DNA concentration of 1.3 μg/ml. Transformation of the circularized DNAs into competent JM109 cells (Stratagene) generated two primary libraries for both A thaliana and yeast.

EXAMPLE 2

Assembly of Secondary Telomeric Libraries

Colonies representing both primary libraries (yeast primary libraries contained 474 (pSDC12) and 541 (pSDC13) colonies (see Table 1); A. thaliana primary libraries contained 5500 (pSDC12) and 5700 (pSDC13) colonies) were scraped from agar plates, grown en masse in liquid culture, and infected at a multiplicity of infection of 10 with the M13 helper phage rv1 (Levinson et al., J. Mol. App. Genet. 2:507-517 (1984)). The infected cultures were diluted 100-200 fold, grown 10-14 hr at 37° C., and phage particles were purified from the supernatants as described in Levinson et al., supra (1984). Phenol extraction and ethanol precipitation of the purified phage yielded single-stranded DNA representing each primary library.

For both A. thaliana and yeast, the single-stranded DNAs from the two primary libraries were mixed in equimolar amounts and allowed to anneal in 25 mM K+ phosphate buffer pH 6.8 at 42° C. for 3 hr (approximately 10 X $C_ot_{\frac{1}{2}}$ for the A. thaliana primary libraries). Cross-hybridizing single-stranded DNA molecules were isolated as partially double-stranded DNAs using hydroxylapatite chromatography as follows: 0.2 g of hydroxylapatite (BioRad HTP) hydrated in 100 mM K+ phosphate buffer, pH 6.8, and heated to 100° C. for 30 min (Martinson et al., Anal. Biochem. 61:144-154 (1974)) was equilibrated in 25 mM K+ phosphate buffer, pH 6.8, and poured into a water-jacketed column (0.7 cm inner diameter) that was maintained at 42° C. The DNA hybridization solutions were diluted into 0.5 ml of 25 mM K+ phosphate buffer, pH 6.8, and applied to the column. Single-stranded DNA was eluted by washing the column with 8 ml of 100 mM K+ phosphate, pH 6.8, at 42° C. followed by 3 ml of the same buffer at 50° C. Partially double-stranded DNAs were eluted from the column with 2-4 ml of 200 mM K+ phosphate buffer, pH 6.8, at 50° C. The fractions containing the partially double-stranded plasmids were concentrated by sec-butanol extraction followed by a chloroform extraction; the phosphate buffer was exchanged with 10 mM Tris-HCl pH 8.0, 1 mM EDTA, 100 mM NaCl using Sephadex G-50 (Pharmacia) spin columns, and the DNA was ethanol-precipitated. Secondary libraries were formed by transforming HB101 with the purified cross-hybridizing single-stranded plasmids using the protocol developed by Michael Scott (personal communication).

The A. thaliana secondary library was screened to identify abundant nontelomeric repetitive DNA clones by colony hybridization (described below) using a mixed probe containing the inserts of pARR12, pARR20-1, pKDR1, and pKDR2. Colonies which did not hybridize to this mixed probe were saved in ordered arrays in 96 well microtiter dishes at −80° C. in LB media containing 15% glycerol.

For characterizations of the yeast primary and secondary libraries, colony hybridizations were performed using nitrocellulose filters according to the protocols of Grunstein et al., PNAS USA 72:3961-3965 (1975) with the following exceptions: the hybridizations (using poly d(CA/GT) probe) were carried out in 1 M NaCl, 10% dextran sulfate, 1X P Buffer (New England Nuclear, Gene Screen protocols), and 25 μg/ml E. coli DNA at 60°-65° C. The filters were washed in 2X SSC, 0.5% SDS at 50°-55° C. The A. thaliana secondary library was gridded out on large (22×22 cm) agar plates and transferred to uncharged nylon membranes (BioTrans, ICN). The colonies were lysed by autoclaving the membranes for 1 min, and the hybridizations (using pAtT4 insert probe) were carried out at 65° C. using 1 M NaCl, 10% dextran sulfate, 1% SDS, 25 μg/ml tRNA, and a probe concentration of $10^5$ cpm/ml. The filters were washed at 60° C. with 0.2X SSC, 0.1% SDS.

EXAMPLE 3

Screening of Secondary Telomeric Libraries

To screen the A. thaliana secondary library, liquid cultures inoculated from the microtiter dishes were pooled in groups of 5-6 and the plasmid DNAs purified by the alkaline lysis miniprep procedure (Ausubel et al., supra (1987)). The plasmid pools were radiolabeled by nick translation using $^{32}P$-dCTP (New England Nuclear) and used to probe genomic Southern blots (HaeIII digests) of A. thaliana nuclear DNA which had been previously digested with Bal31 nuclease for 0, 7, and 30 min under the following conditions:

High molecular weight A. thaliana nuclear DNA was digested with 0.25 U/ml Bal31 nuclease at 30° C. at a DNA concentration of 10 μg/ml in 12 mM $CaCl_2$, 24 mM $MgCl_2$, 0.2 M NaCl, 20 mM Tris-HCl pH 8.0, 1 mM EDTA, and 100 μg/ml BSA. Modifications of these parameters used for Bal31 digestion of Z. mays and human genomic DNA are indicated in the appropriate figure legends. Reactions were stopped at the indicated times by addition of EGTA to a final concentration of 20 mM, extracted with phenol and chloroform, and precipitated with ethanol.

Southern blotting and hybridization were carried out with nylon filters (GeneScreen, NEN) using the UV cross-linking procedure of Church and Gilbert, *PNAS USA* 81:1991–1995 (1984)). Generally, hybridizations were done in 0.5 M NaHPO$_4$, pH 7.2, 7% SDS, 1 mM EDTA, and 1% BSA (Church and Gilbert, supra (1984)) at 50° C. using a probe concentration of 10$^6$ cpm/ml. Filters were washed under the following conditions: Low stringency=2X SSC, 1% SDS at 60° C.; high stringency=0.2X SSC, 0.1% SDS at 60° C.

In this case, the blots were washed under in 2X SSC, 1% SDS at 55° C. Plasmid pools that hybridized to Bal31 nuclease-sensitive bands or bands that ran at the limit of mobility were split into individual clones to identify potential telomeric clones.

EXAMPLE 4

Identification of pAtT4 Telomeric Insert

To identify *A. thaliana* telomeric clones, the screening procedure described in Example 3 was used. One clone, designated pAtT4, was found which hybridized to exonuclease-sensitive restriction fragments. This plasmid was isolated as a stable derivative of a larger plasmid that suffered spontaneous deletions.

Figures 2A, 2B:
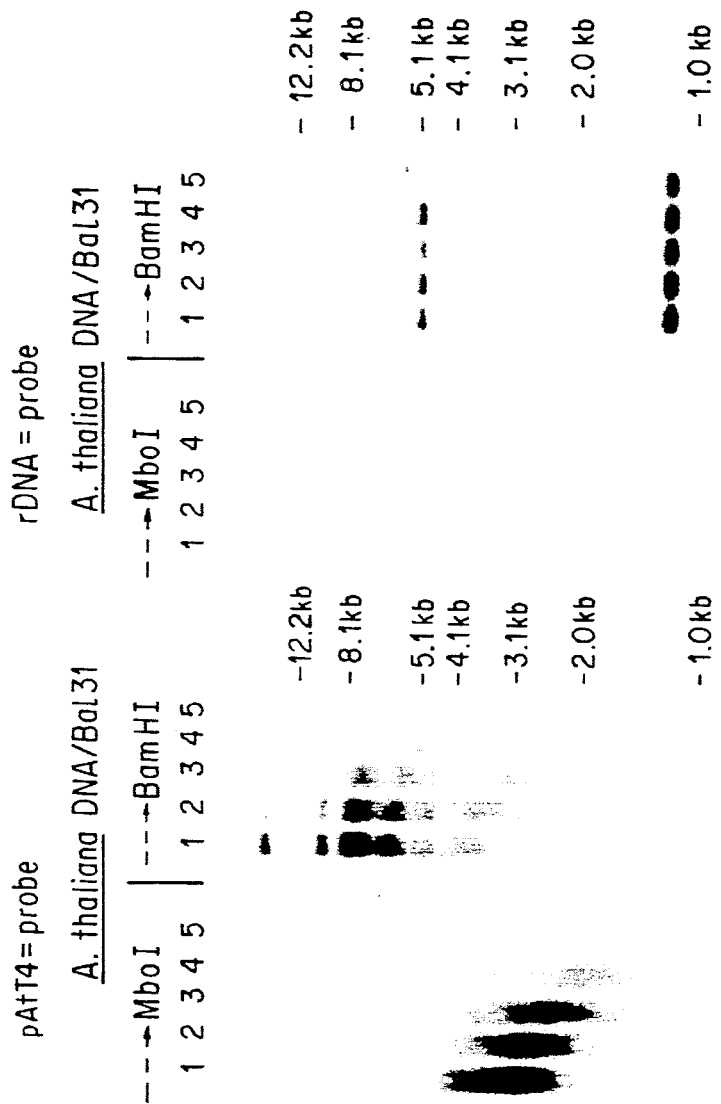
FIG. 2(A) shows *A. thaliana* nuclear DNA treated with Bal31 for 0 (lane 1), 5 (lane 2), 15 (lane 3), 30 (lane 4), or 50 minutes (lane 5), and subsequently digested with MboI (left lanes) or BamHI (right lanes). The DNA was sized-fractionated by electrophoresis through a 0.8% agarose gel and transferred to a nylon membrane. The membrane was probed with radiolabeled pAtT4 and washed at high stringency.
FIG. 2(B) shows the membrane shown in (A), rehybridized with radiolabeled pARR16, an *A. thaliana* rDNA clone, and washed at high stringency.

FIG. 2 shows a Southern blot of Bal31-treated *A. thaliana* nuclear DNA which was probed with radiolabeled pAtT4. The lanes at the left in FIG. 2A contain Bal31-digested nuclear DNA which was subsequently cut with MboI. In the non-Bal31-treated lane, pAtT4 hybridized to a smear representing restriction fragments ranging from 2.0 to 5.0 kb in length. The size and intensity of the heterodisperse MboI band decreased upon increasing exonuclease treatment. The rate of exonuclease digestion was linear and approximately 2.5 kb of sequence had to be removed to eliminate most of the pAtT4 hybridization.

The righthand lanes in FIG. 2A show the hybridization pattern of pAtT4 to BamHI-digested Bal31-treated genomic DNA. In this case, the hybridization signal was resolved into several higher molecular weight bands; these bands were still diffused, indicating that the probe hybridized to a collection of restriction fragments that were heterogeneous in size. The BamHI bands become smaller and eventually disappeared with increasing Bal31 digestion.

To demonstrate that the exonuclease sensitivity of pAtT4 homologous sequences was not a property of genomic sequences in general, the filter shown in FIG. 2A was reprobed with *A. thaliana* ribosomal DNA. The results (FIG. 2B) show that the rRNA gene probe hybridized to several bands, none of which shifted mobility due to exonuclease treatment.

EXAMPLE 5

Sequencing of pAtT4 Telomeric Insert

The pAtT4 insert was sequenced by the dideoxy method using double-stranded template following the protocols described in Ausubel et al., supra (1987). The simple sequence insert template caused pausing of the reverse transcriptase, making it difficult to read sequence far from the primer; for this reason, both strands of the insert were not sequenced in their entirety. The sequence of the telomeric repeats was confirmed by sequencing pAtT4 using the chemical method of Maxam and Gilbert, *Meth. Enzymol.* 65:499–560 (1980).

The DNA sequence of pAtT4 insert is shown in FIG. 4. The insert is composed almost entirely of tandemly repeated blocks of the sequence 5'-[CCCTAAA]-3'. Two variant repeats, 5'-[CTCTAAA]-3', were found in tandem in the middle of the insert. The simple sequence repeated DNA abuts the blunt end cloning site of the vector (noted as ½ HincII in FIG. 4); this end of the insert corresponds to the terminus of the chromosome. It should be kept in mind, however, that since the genomic DNA was initially treated with Bal31 to remove a small number of nucleotides from the ends, before the cloning was performed, any DNA structures (such as foldbacks, nicked strands) at the extreme terminus were not preserved in the pAtT4 insert.

From the telomeric end of the insert, the tandemly repeated sequence extends 386 bp, comprising 55 complete repeat units. The orientation of the repeats is such that the C-rich strand points towards the centromere when read in the 5' to 3' direction. In addition, the insert contains 17 nucleotides of a nonrepeat flanking sequence which includes the MboI site used to clone the terminal restriction fragment.

The discrepancy between the size of the pAtT4 insert (403 bp) and the telomeric MboI restriction fragments detected on Southern blots (2.5–5.0 kb) (see FIG. 2A) is most likely due to internal deletion of the telomeric repeats during propagation of the plasmid. Consistent with this interpretation is the fact that pAtT4 was isolated as a stable derivative of a larger plasmid which suffered spontaneous deletions. Similar instability of simple sequence telomeric repeat clones from Trypanosomes has been noted (see Blackburn et al., *Cell* 36:447–457 (1984)).

EXAMPLE 6

Representation of pAtT4 Homologous Clones in the *A. thaliana* Primary and Secondary Libraries The representation of telomeric clones in the *A. thaliana* primary and secondary libraries was determined by colony hybridization using the purified insert of pAtT4 as a probe. Approximately one out of 5000 clones in each amplified primary library hybridized to the pAtT4 insert probe (frequency of $2 \times 10^{-4}$). Since each primary library was composed of approximately 5500 members, this result suggests that each of the original primary libraries contained a single telomeric clones. The secondary library, on the other hand, contained five out of a total of 765 clones which hybridized to the pAtT4 insert probe (frequency of $6.5 \times 10^{-3}$). The assembly of the secondary library resulted in a roughly 30-fold enrichment for telomeric clones relative to the primary libraries.

EXAMPLE 7

Figure 1:
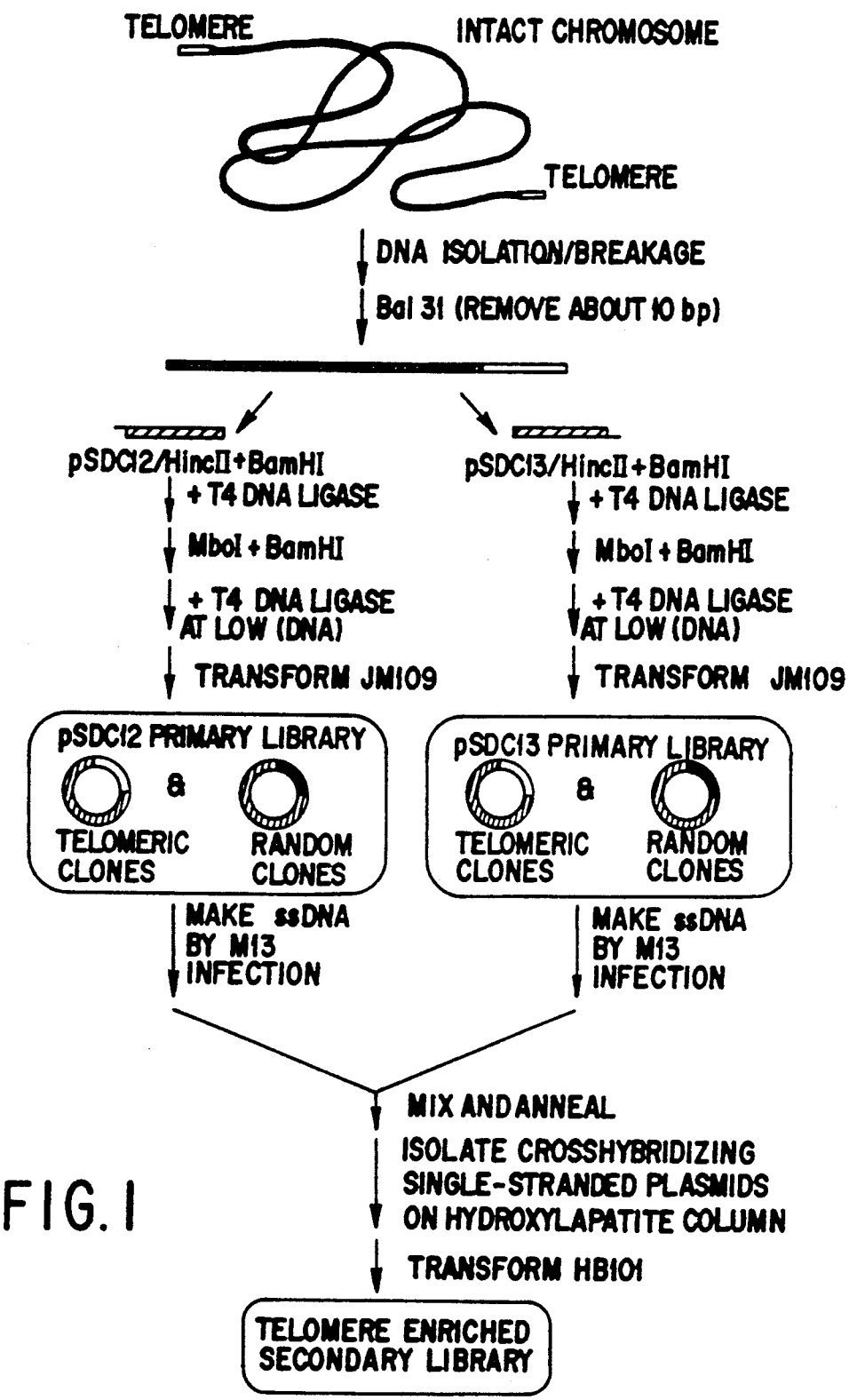
FIG. 1 shows schematically the procedure used for constructing the primary telomeric libraries which produce random, non-telomeric clones and telomeric clones, and the procedure used for enriching for the telomeric clones produced by the two independent primary libraries.

Isolation of Telomeric DNA Sequences from Yeast Using the Enrichment Strategy To determine the effectiveness of the telomeric cloning and enrichment strategy outlined in FIG. 1, an experiment was undertaken to clone yeast telomeric sequences by this method. The results are presented in Table One.

TABLE ONE

| Type of Library | Vector | Members | % Inserts | Members w/ Inserts | # CA/GT | Freq |
|---|---|---|---|---|---|---|
| Primary | pSDC12 | 474 | 50% | 240 | 4 | 0.017 |
| Primary | pSDC13 | 541 | 65% | 350 | 6 | 0.017 |
| Secondary "A" | — | 164 | 100% | 164 | 28 | 0.17 |

TABLE ONE-continued

| Type of Library | Vector | Members | % Inserts | Members w/ Inserts | # CA/GT | Freq |
|---|---|---|---|---|---|---|
| Secondary "B" | — | 134 | nd | <134 | 27 | 0.20 |

The type (primary versus secondary) and size (number of member clones) of the yeast libraries are indicated. Secondary "A" and "B" denote two independently assembled secondary libraries. The % insert was estimated from the study of 20 randomly selected clones (nd=not determined). #CA/GT refers to the number of clones which hybridized to a radiolabeled poly d(CA/GT) probe, as determined by the colony hybridization method. The frequency of poly d(CA/GT) hybridizing clones in each library (Freq) was calculated by dividing #CA/GT by the number of members with inserts.

The pSDC12 and pSDC13 yeast primary libraries contained 240 and 350 clones with inserts, respectively. Approximately one out of sixty clones in both yeast primary libraries hybridized to a poly d(CA/GT) probe that cross-hybridized to the yeast telomeric sequence $(C_{1-3}A)_n$, as well as short stretches of $(CA)_n$ found in the chromosome arms (Walmsley et al., *PNAS USA* 82:506–510 (1983)).

The following observations indicate that most of the poly d(CA/GT) hybridizing clones contained telomeric sequence inserts: (1) 9 out of 10 clones had the insert orientation predicted for cloning of telomeric restriction fragments (with asymmetric C-rich and G-rich strands) into the pSDC12 and pSDC13 complementary vectors, (2) sequencing of one pSDC13 clone showed that the $(C_{1-3}A)_n$ sequence abuts the blunt end cloning site of the vector, (3) Southern blot experiments indicated that at least three clones contained inserts which cross-hybridized with telomere flanking sequences (data not shown).

Two separate secondary libraries (designated A and B) were assembled from the primary yeast libraries as described in FIG. 1. As shown in Table One, the frequency of clones hybridizing with the poly d(CA/GT) probe was approximately 0.2 in both secondary libraries, indicating that a ten-fold enrichment in clones that hybridized to the poly d(CA/GT) probe was achieved.

EXAMPLE 8

Identification of a Telotrisomic RFLP by the Telomeric Clone pAtT4

To determine if pAtT4 would identify a telotrisomic RFLP, Southern blots of genomic DNA were prepared from telotrisomic mutant Tr5A and wild type disomic plants. Genomic DNA from the *A. thaliana* Landsberg telotrisomic mutant and its disomic silbings was prepared by the miniprep procedure of Dellaporta et al., *Plant Mol. Biol. Rptr.* 1:19-21 (1983). One feature of telotrisomic plants that is of particular use in this experiment is that both disomic and telotrisomic plants appear in the progeny after selfing telotrisomic parents. Therefore, the telotrisomic progeny should be isogenic with their disomic siblings except for the presence of the extra telocentric chromosome. Moreover, since the telocentric chromosome is free to recombine with the full length chromosomes, and the telotrisomic stocks are maintained by selfing mutant plants, the only qualitative difference between the genomes of the telotrisomic and the disomic progeny should be the new telomere.

Telotrisomic and normal disomic plants are distinguished on the basis of gross morphology. Disomic plants are generally larger and have broad leaves while Tr5A telotrisomics are semi-dwarf plant with narrow and slightly serrated leaves. There is some overlap in the phenotypic norms; in particular, individual diploid plants that are growing slowly will occasionally be identified incorrectly as telotrisomic. It is unlikely, however, that telotrisomic progeny will be mistaken for disomics.

As shown in FIG. 3B, pAtT4 hybridized to a 15 kb DraI restriction fragment in the Tr5A genome that is absent from the disomic genome. This novel restriction fragment corresponds to the functional telomere that was added next to the centromere.

The experiment shown in FIG. 3B was repeated using DNA isolated from 14 individual progeny plants derived from selfing a single Tr5A parent. Of the 14 plants, 9 were identified as disomics; none of these plants contained the polymorphic 15kb DraI marker identified by pAtT4. This result indicates that the RFLP was linked to the new telomere since this telomere is the only genetic marker that can not be crossed away from the telocentric chromosome onto the full length chromosomes. The remaining 5 plants were identified phenotypically as telotrisomics; of these, 3 displayed the telotrisomic pattern defined in FIG. 3B, and 2 displayed the disomic pattern. As expected, the RFLP was only found in plants phenotyped as telotrisomics. The "telotrisomic" plants which did not contain the marker were most likely incorrectly phenotyped disomic plants and not a consequence of recombination between the new telomere and the polymorphic marker since such a recombination event was not detected from study of the disomic siblings.

The correlation between the presence of the new telomere and the pAtT4 15 kb DraI polymorphic marker, in conjunction with the exonuclease sensitivity of the pAtT4 homologous genomic sequences, argues convincingly that pAtT4 hybridized to telomeric sequences in *A. thaliana*.

Another feature of the blot shown in FIG. 3B is of interest. The heterodisperse bands in the Tr5A lane are slightly smaller than the corresponding bands in the disomic lane, indicating that the telomeres in the mutant are smaller. This size difference is not surprising since telomeres in lower eukaryotic systems are known to be dynamic structures which change length depending on the genetic background and growth conditions of the organism.

EXAMPLE 9

Isolation of Plant Centromeres Using Cloned Plant Telomeres

Once a telotrisomic RFLP is identified, a genomic library may be constructed to clone the restriction fragment representing the CEN-telomere fusion. Genomic DNA from the telotrisomic mutant is treated briefly with the exonuclease Bal31 to generate blunt ends at the telomere, as was done in the telomere cloning strategy (see FIG. 1). The end-repaired genomic DNA is then digested with the restriction endonuclease which defines the RFLP, and the population of DNA molecules corresponding to the size of RFLP isolated. The size-selected DNA is cloned into a circular episomal yeast vector that carries a functional CEN and ARS. The yeast vector-host system is preferably used because of its tolerance for long, repetitive DNA inserts (see Burke et al., Science 236:806-812 (1987)). The desired CEN-telomere clone may be identified in the library by hybridization with the isolated *A. thaliana* telomere. Alternatively, an *E. coli* vector-host system can be used.

EXAMPLE 10

Figure 11A:
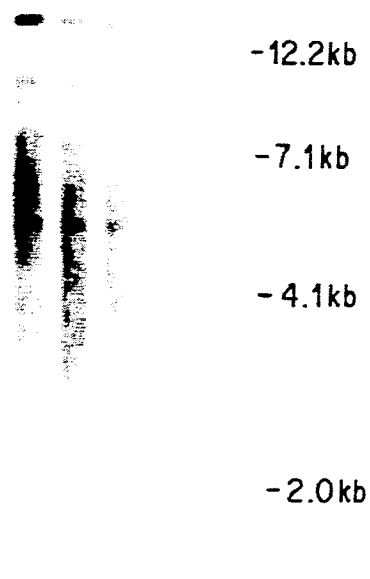
FIG. 11 shows that *A. thaliana* telomeric repeats cross-hybridize to non-telomeric sequences at reduced stringencies. *A. thaliana* nuclear DNA was treated with Bal31 for 0 (lane 1), 5 (lane 2), 15 (lane 3), 30 (lane 4), or 50 minutes (lane 5) and subsequently digested with HindIII. The DNAs were then size fractionated by electrophoresis through a 0.8% agarose gel and transferred to a nylon membrane. The membranes were probed with radiolabeled pAtT4 insert DNA and washed at either high stringency ((A) 0.1X SSC, 0.1% SDS @60° C.) or low stringency ((B) 2X SSC, 1% SDS @60° C.).
Figure 11B:
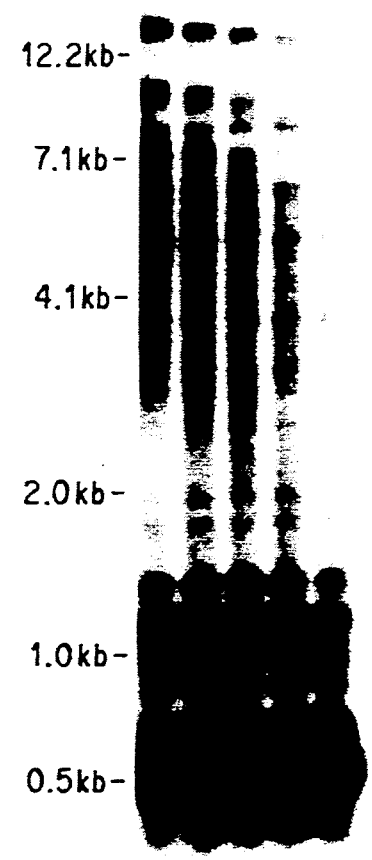

*A. thaliana* Telomeric Repeats Cross-hybridize with Non-telomeric Sequences at Reduced Stringency The *A. thaliana* telomeric clone pAtT4 hybridized to both telomeric and non-telomeric restriction fragments under reduced stringency conditions. FIG. 11 shows HindIII Southern blots of nuclease Bal31-treated *A. thaliana* nuclear DNA probed with radiolabeled pAtT4 and washed at different stringencies. Under high stringency conditions (FIG. 11A) the pAtT4 probe recognized dispersed, exonuclease-sensitive bands characteristic of telomeric restriction fragments. A few faint bands, which were insensitive to the exonuclease treatment, were also detected by the telomeric probe under high stringency conditions. However, when the stringency of hybridization was reduced, a different hybridization pattern was seen. The Bal31-sensitive telomeric signals were still present, but the majority of the hybridization signal corresponded to several discrete, exonuclease-insensitive bands (FIG. 11B). Most prominent among these exonuclease-insensitive signals was a band corresponding to HindIII restriction fragments of approximately 500 bp.

These data indicate that the *A. thaliana* genome contains sequences resembling telomeric repeats which are not located at the chromosomal termini. Since the most extensive nuclease Bal31 digestion (FIG. 11A & B; lane 5) removed approximately 2.5 kb from the chromosome ends but did not alter the electrophoretic migration of the cross-hybridizing bands, this indicates that most of the exonuclease-insensitive telomere-similar sequences are located farther than 2.5 kb from the chromosomal termini. The fact that the telomere-similar sequences were only significantly detected under reduced stringency conditions suggests that these sequences contain either short stretches of telomeric repeats or repeats which are similar but not identical to the [TTTAGGG] telomeric motif.

EXAMPLE 11

Isolation and Characterization of an *A. thaliana* Telomere-similar Sequence Clone To determine the nature of the telomere-similar sequences, several clones containing these sequences from *A. thaliana* genomic library (Columbia ecotype) were isolated using the insert of the telomeric clone pAtT4 as hybridization probe.

*A. thaliana* nuclear DNA (2 μg) was digested with Bal31 nuclease to remove approximately 30 bp from the chromosomal termini (DNA concentration=10 μg/ml, enzyme concentration=0.25 U/ml, 30° C., 60 seconds). The cloning vector pSDC13 was prepared by sequential digestion with HincII and BamHI, and treated with calf intestinal phosphatase to remove 5' phosphates. The nuclease-treated DNA was then ligated to 0.6 μg of prepared vector using T4 DNA ligase (DNA concentration—130 μg/ml, enzyme concentration=20,000 U/ml, 22° C.). The ligation products were digested with BamHI and size-fractionated by agarose gel electrophoresis (0.7%, low melting agarose). Linear vector-genomic DNA chimeras of 11-15 kb were purified and circularized with T4 DNA ligase (DNA concentration=0.5 μg/ml, enzyme concentration=130 U/ml, 4° C.). The circularized DNAs were then transformed into K802 recA (*) using the protocol developed by Michael Scott (personal communication).

Clones cross-hybridization with the pAtT4 insert were identified by colony hybridization (Grunstein and Hogness, 1975). Colonies were grown on Colony/Plaque Screen (NEN) filters and lysed by autoclaving the membranes for 1 minute. Hybridization was carried out at 60° C. using 1 M NaCl, 10% dextran sulfate, 1% SDS, 25 μg/ml tRNA, and a probe concentration of $10^5$ cpm/ml. The filters were washed at 60° C. with 0.2X SSC, 0.1% SDS.

Figure 12:
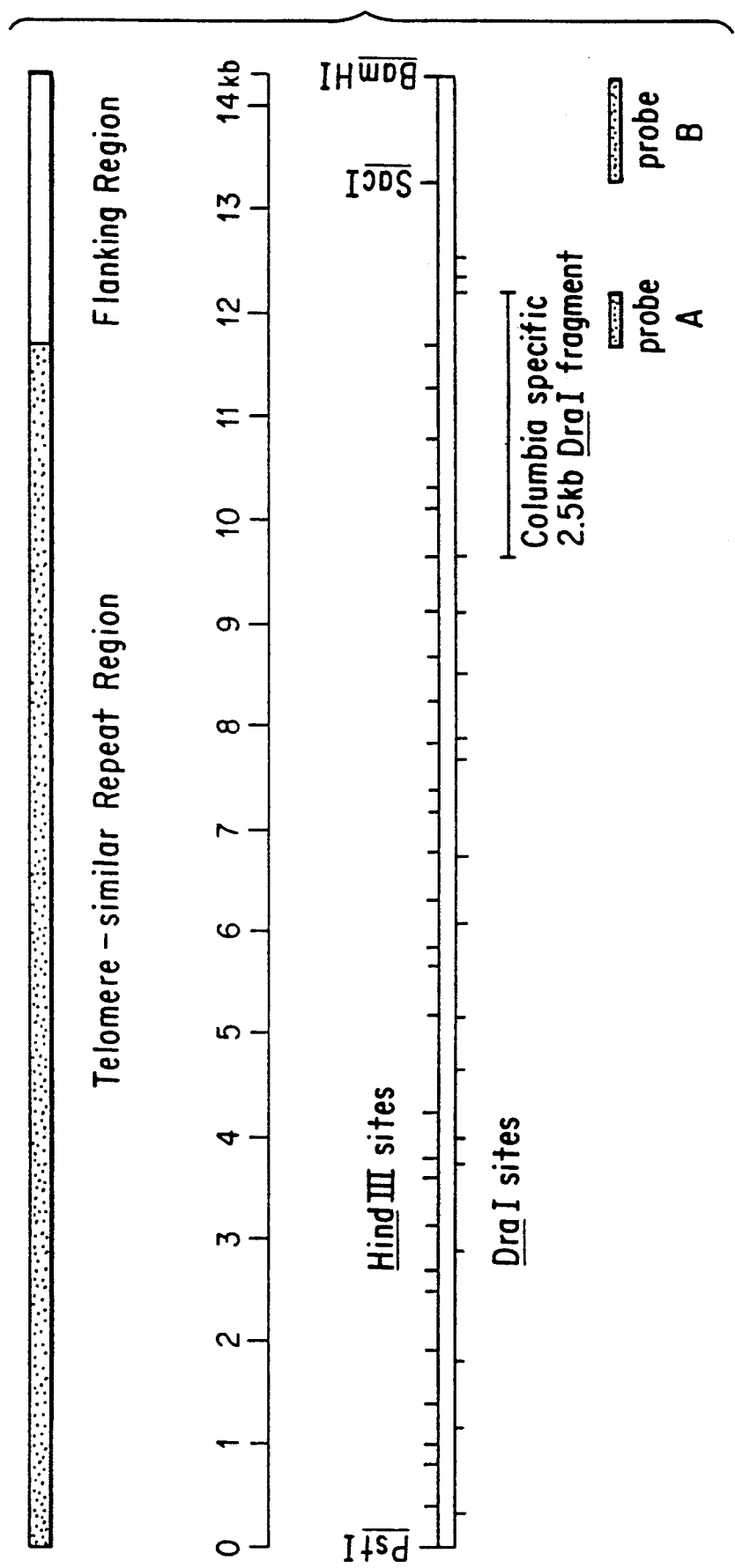
FIG. 12 shows the molecular organization of telomere-similar clone pAtT12. The 14.3 kb insert of pAtT12 contains two domains: an 11.7 kb region containing highly reiterated telomere-similar DNA sequences, and a 2.6 kb "flanking region" devoid of telomere-similar sequences. The restriction map of the insert, shown at the bottom of the figure, illustrates the high density and periodic distribution of HindIII and DraI sites in the telomere-similar region. The insert was cloned into pSDC13 as a BamHI to blunt end fragment; the PstI site shown at the left hand end of insert is derived from the vector polylinker. The hybridization probes (probes A and B) and the 2.5 kb Columbia-specific DraI fragment used in the RFLP mapping experiments are shown at the lower right.

The inventors analyzed the structure of one of the clones, designated pAtT12. A restriction map of the pAtT12 insert is shown in FIG. 12. Southern blot experiments indicated that the 2.6 kb region residing at the righthand end of the insert (referred to as "flanking region") does not contain telomere-similar sequences (data not shown). The remaining 11.7 kb of the 14.3 kb insert is comprised of many short restriction fragments, most of which cross-hybridized with the telomeric probe. The high density and relatively even spacing of HindIII and DraI restriction sites in the telomere-similar region suggests this region is composed of short repeat elements arranged in tandem. The majority of HindIII sites are spaced approximately 500 bp apart; however, there are several smaller intervals of ~180 bp and a large 1 kb interval. The 1 kb and ~500 bp HindIII fragments cross-hybridized with the telomeric probe, while the ~180 bp HindIII fragments did not (data not shown).

Figure 13:
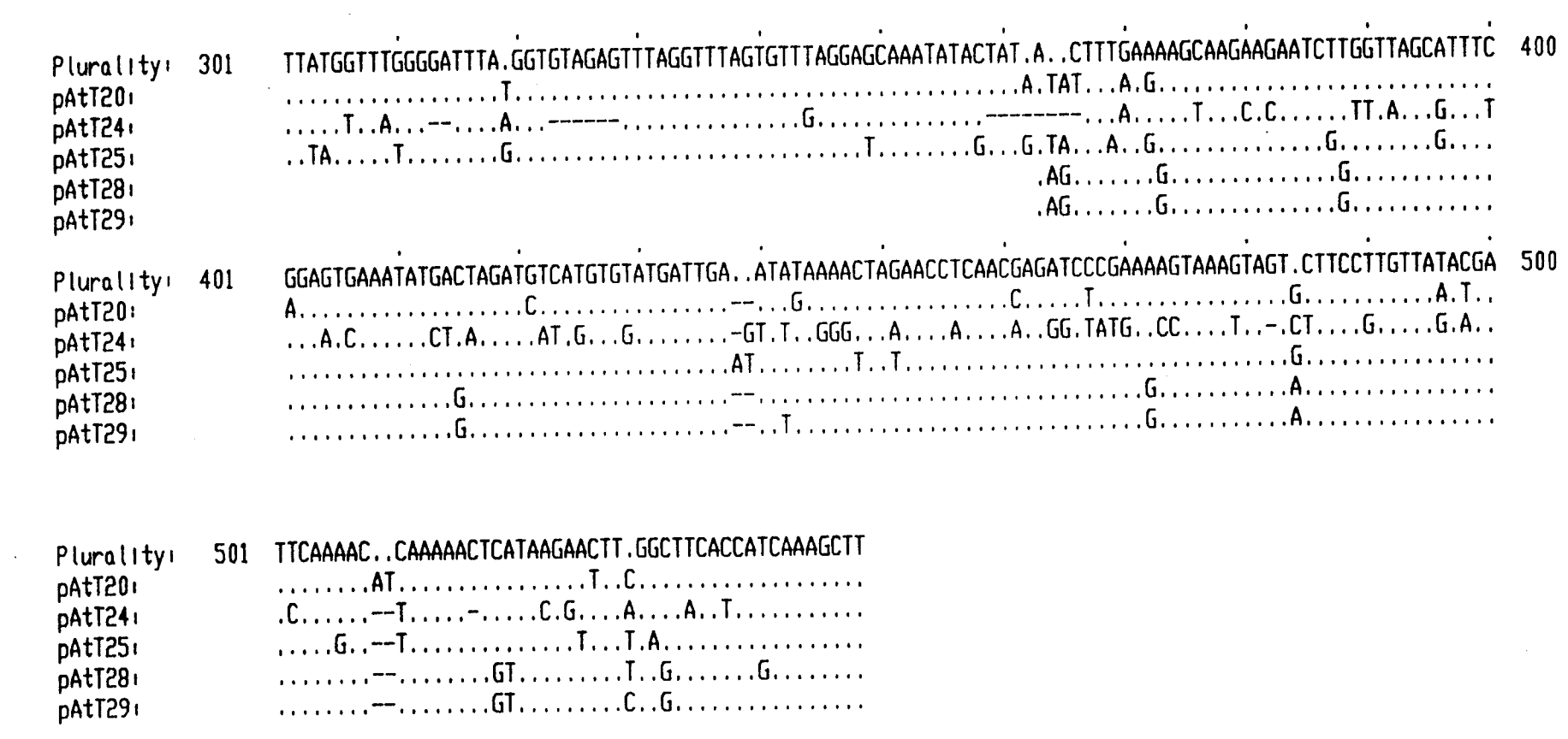

To understand the structure and organization of sequences in the telomere-similar region of pAtT12, the inventors determined the DNA sequence of three ~500 bp and two ~180 bp HindIII restriction fragments from this region (FIG. 13). The larger HindIII fragments range in size from 483 to 527 bp. These sequences display 78-89% similarity with each other, and contain a 150 to 200 bp simple-sequence domain (nucleotides 150-350 in FIG. 13) which resembles the [TTTAGGG]$_n$ structure of *A. thaliana* telomeres. The variable length of the simple-sequence region accounts, in part, for the different sizes of the repeat units. Several identical matches to the telomeric motif are present in the simple-sequence region but most of the domain is composed of imperfect telomere-similar repeats. The degenerate nature of the telomere-like repeats explains why the telomeric clone pAtT4 hybridizes strongly to these repeats only under low stringency conditions. The ~180 bp HindIII fragments are closely related to the ~500 bp element but lack the telomere-similar domain.

The DNA sequence and restriction mapping data indicate that the pAtT12 insert is primarily composed of many copies of related telomere-similar repeats. The irregularities in the spacing of the HindIII restriction sites seen in FIG. 12 are caused by the variable size of the repeat units. In addition, the ~500 bp telomere-similar repeats are interspersed with closely related ~180 bp repetitive elements which lack a telomere-similar domain.

The pAtT12 insert represents the organization of a considerable fraction of telomere-similar sequences in the *A. thaliana* genome. The size of the HindIII repeats corresponds to the prominent HindIII band at approximately 500 bp seen on genomic Southern blots (FIG. 11B). The other exonuclease-insensitive HindIII bands seen in FIG. 11B may represent repeat multimers or related repeats of different size.

EXAMPLE 12

Chromosomal Location of pAtT12 Insert Sequences

Highly reiterated tandem repeats are frequently located in constitutively condensed regions of the chromosome called heterochromatin (John, "The Biology of Heterochromatin" In: Heterochromatin: Molecular and Structural Aspects, (ed. Verma, Ram S.), Cambridge University Press, Cambridge (1988)). *A. thaliana* chromosomes contain heterochromatic regions around all five centromeres and some of the telomeres (Schweizer et al., *Arab. Inf. Serv.* 25:27–34 (1987)), features common to most higher eukaryotic organisms. The inventors then decided that the chromosomal location of the telomere-similar repetitive DNA array contained in the pAtT12 insert should be determined.

Chromosomal localization of the pAtT12 insert sequences was accomplished by following the segregation of RFLP alleles in the progeny of an inter-ecotype (Columbia X Landsberg) cross. Since pAtT12 was isolated from a library constructed with Columbia ecotype DNA, the inventors searched in the flanking region of the pAtT12 insert for a probe which hybridized to a single-copy Columbia-specific restriction fragment which was absent or polymorphic in the Landsberg ecotype parent. The inventors identified a 470 bp HindIII-DraI fragment (probe A; see FIG. 12) which hybridized to a 2.5 kb DraI restriction fragment present only in genomic DNA from the Columbia ecotype parent. The position of the corresponding 2.5 kb DraI fragment in pAtT12 is noted in FIG. 12. A panel of Southern blots containing DraI digested genomic DNA corresponding to the F2 segregants of the inter-ecotype cross were hybridized with probe A and, based on the resulting hybridization pattern, a genetic map position for the pAtT12 telomere-similar repetitive array was assigned relative to other RFLPs and genetic markers.

Figure 14:
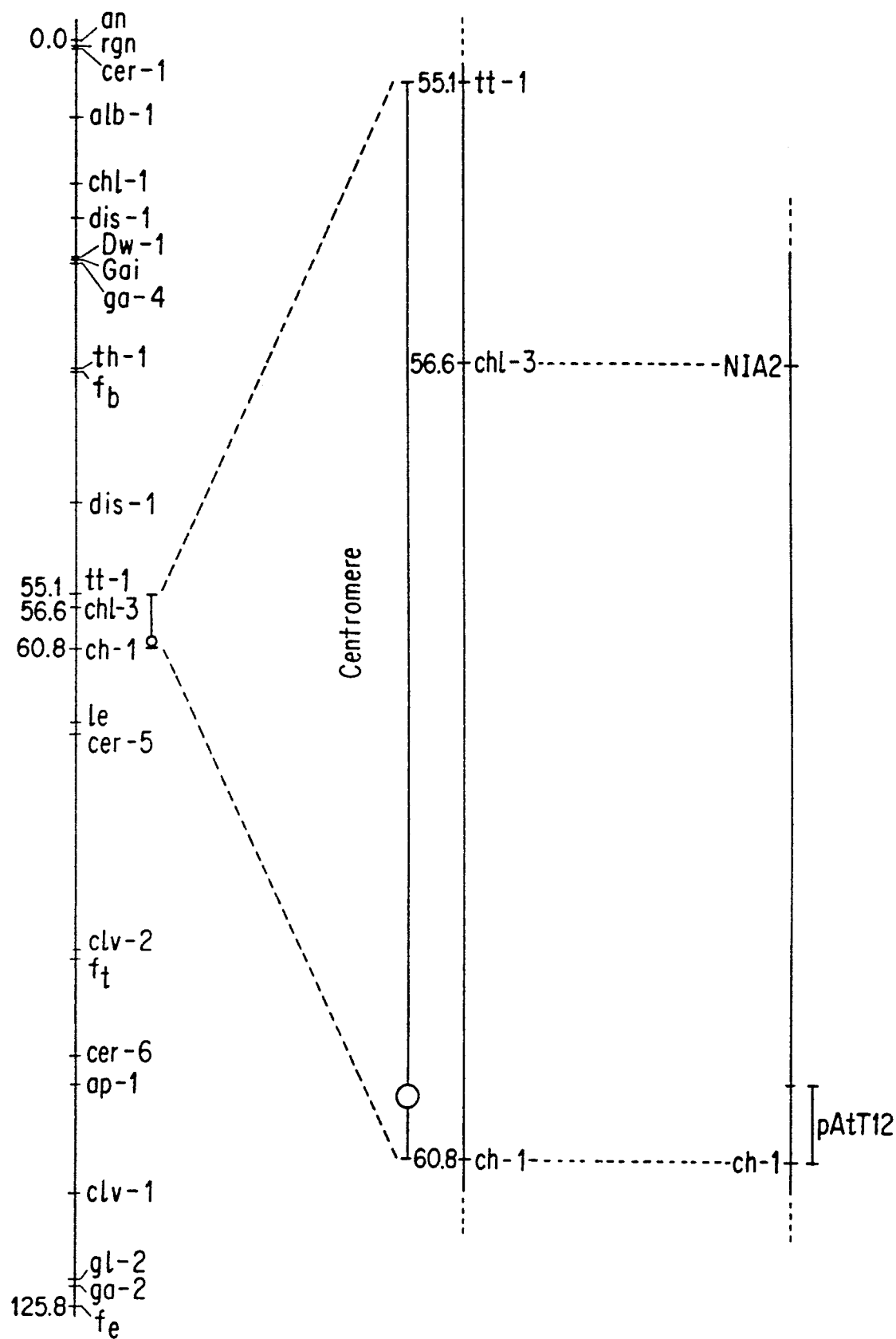
FIG. 14 shows that the pAtT12 insert was derived from the centromere region of chromosome 1. The entire genetic map of *A. thaliana* chromosome 1

As shown in FIG. 14, the pAtT12 insert was derived from genomic sequences which reside in the middle of chromosome 1, in the vicinity of the centromere. The pAtT12 RFLP is closely linked to several other RFLP markers and the morphological marker ch-1. The order of these markers cannot be unambiguously defined by the MAPMAKER program used to assemble the map. To construct the simplified region of the RFLP map shown in FIG. 14 a constraint was placed on the order of ch-1 and NIA2 by correlation with the genetic map. The NIA2 RFLP is defined by a nitrate reductase structural gene and is assumed to correspond to the chl-3 (reduced nitrate reductase activity leading to chlorate resistance) genetic marker (Cheng et al., 1988). Given this assumption, the most likely map position for the pAtT12 insert DNA is within 1 cM of ch-1 in the interval between ch-1 and NIA2.

Koornneef and co-workers have determined that centromere 1 is closely linked to the morphological marker ch-1, and resides in the genetic interval between the tt-1 and ch-1 marker (Koornneef, *Genetica* 62:33–40 (1983); Koornneef and Van der Veen, *Genetica* 61:41–46 (1983)). Based on these data, it can be seen that the telomere-similar repetitive array cloned in pAtT12 is associated with the centromere heterochromatin of chromosome 1.

EXAMPLE 13

The pAtT12 Insert Flanking Region Contains a Repetitive DNA Element that Cross-hybridizes to Sequences in the Centromere Region of Chromosome 5

The flanking region of the pAtT12 insert contains moderately repeated sequences. As shown in FIG. 15, a 1 kb SacI fragment from the right-hand end of the flanking region (probe B; see FIG. 12) hybridized to approximately five bands on genomic Southern blots.

The centromere-proximal location of the pAtT12 insert sequences led the inventors to investigate whether the cross-hybridizing restriction fragments seen in FIG. 15 are located in other centromere regions. Probe B was used, which identifies three DraI RFLPs (two Landsberg-specific [A & B], and one Columbia-specific [C]; see FIG. 15) to hybridize Southern blots of F2 segregant genomic DNAs. The resulting hybridization patterns were analyzed and the map positions of the RFLP markers were determined.

The Landsberg-specific RFLP B and the Columbia-specific RFLP C are allelic and mapped to chromosome 1 at the location identified by the Columbia-specific 2.5 kb DraI marker recognized by probe A. The remaining Landsberg-specific RFLP A mapped to the middle of chromosome 5, approximately 14 cM from the morphological marker ttg. On the classical genetic map, the centromere of chromosome 5 lies between the ga-3 and ch-5 genetic loci (Koornneef, Genetic Maps (Cold Spring Harbor: Cold Spring Harbor Labortory Press (1987)), placing the centromere at a genetic distance of 3.9 to 14.3 cM from ttg. Consequently, at least one of the cross-hybridizing bands identified by the repetitive element in the pAtT12 flanking region maps to a different chromosome in the vicinity of a centromere.

EXAMPLE 14

DNA Sequence of the pAtT12 Flanking Region

The DNA sequence of the 2.6 kb flanking region of pAtT12 was determined in order to study the structure of the centromere-linked repetitive element. The sequence of the flanking region, shown in FIG. 16, has two unusual domains. The first domain (nucleotides 319 through 798) is 80% AT-rich and contains several direct repeats. A second AT-rich (66%) direct repeat domain was found between nucleotides 1742 and 2300. The second direct repeat region lies within the 1 kb SacI-BamHI fragment of pAtT12 (probe B) which contains all or part of the centromere-linked repetitive element demonstrated in FIG. 15.

The organization of the larger direct repeats ($\geq 9$ bp) is shown in FIG. 16. Most of the repeat motifs are reiterated only twice, and are frequently superimposed. The repeats units are generally well separated within their direct repeat domain but are limited to one domain or the other. In addition, the flanking region contains several small inverted repeat motifs. The largest palindrome (AGTATGGACCAaCAAA.TTT-GaTGGTCTGTACT) is located from nucleotide 2363 to 2394.

EXAMPLE 15

Homology Between *A. thaliana* Telomere Clone and Telomeric Sequences in More Complex Plants To determine whether the telomeric repeats from *A. thaliana* were homologous to telomeric DNA sequences in other higher plants, Southern blots of genomic DNA were prepared from a variety of plant species. Genomic DNA preparation from all plant species other than *A. thaliana* was performed as described in Ausubel et al., In: *Curr. Prot. Molec. Biol.*, pp. 2.3 (New York: John Wiley & Sons) (1987) and incorporated herein by reference. These DNA sequences were probed with radio-labeled pAtT4 and washed at high stringency (see Ausubel, supra). The probe hybridized to genomic sequences from all plants tested including *Brassica campestris, Brassica carinata, Raphanus sativus* (Radish), *Lycopersicon esculentum* (Tomato), *Nicotiana tabacum* (Tobacco), *Medicago sativa* (Alfalfa), and *Zea mays* (Corn). All of these plant species are dicots with the exception of the monocot *Z. mays*.

*A. thaliana* is a dicot and *Z. mays* represents an evolutionarily diverged plant. Thus, *Z. mays* represented an excellent test vehicle for determining the applicability of the teachings of the present invention to higher plant species.

Figures 5A, 5B:
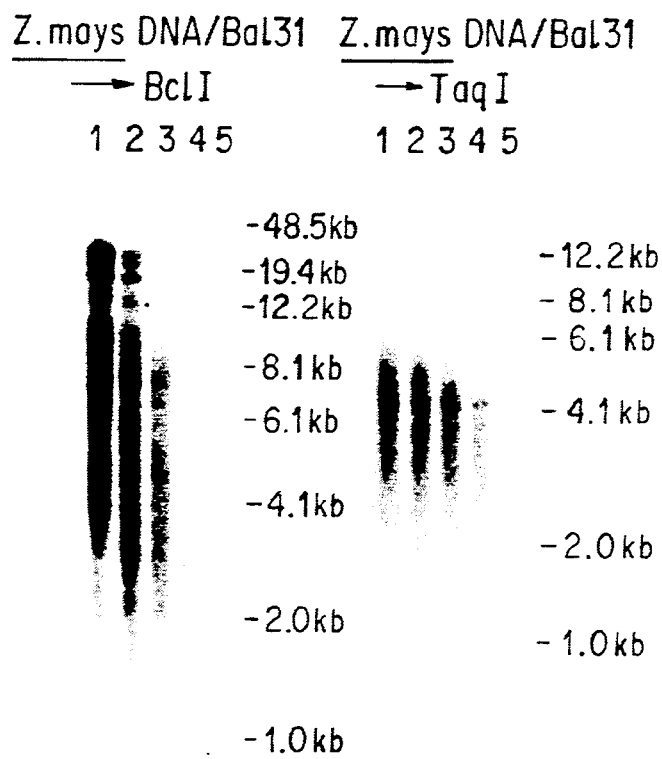
FIG. 5(A) shows *Z. mays* genomic DNA treated with Bal31 [0.5 U/ml] for 0 (lane 1), 15 (lane 2), 35 (lane 3), 60 (lane 4), or 90 minutes (lane 5), and subsequently digested with BclI. The DNA was sized-fractionated by electrophoresis through a 0.7% agarose gel and transferred to a nylon membrane. The membrane was then probed with radiolabeled pAtT4 and washed at high stringency.
FIG. 5(B) shows *Z. mays* genomic DNA treated with Bal31 [0.25 U/ml] for 0 (lane 1), 5 (lane 2), 15 (lane 3), 30 (lane 4), and 50 minutes (lane 5), and subsequently digested with TaqI. The DNA was size-fractionated by electrophoresis through a 0.8% agarose gel and transferred to a nylon membrane. The membrane was then probed with radiolabeled pAtT4 and washed at high stringency.

To determine if the pAtT4 cross-hybridizing sequences in the *Z. mays* genome were located at the telomeres, high molecular weight *Z. mays* genomic DNA was treated with Bal31 for various lengths of time, digested with the restriction endonuclease BclI, size fractionated, and transferred to a nylon membrane. The filter was then probed with pAtT4 and the results are shown in FIG. 5A.

The pAtT4 hybridization pattern includes several bands larger than 14 kb and a collection of incompletely resolved heterodisperse bands of lower molecular weight. The bands become less intense and display increased electrophoretic mobility upon increasing Bal31 treatment. A faint 8 kb band that did not change in size during exonuclease digestion can also be seen in FIG. 5A, demonstrating that sensitivity to Bal31 digestion is not a property of all genomic sequences.

This experiment indicates that *A. thaliana* telomeric repeats cross-hybridize to telomeric sequences in *Z. mays*.

EXAMPLE 16

Cross-Hybridation of *A. thaliana* Telomere Clone to Telomeric Sequences in the Human Genome Southern blots of the genomic DNA prepared from some well-studied animal model systems were probed with pAtT4 to determine if the *A. thaliana* telomere repeat would cross-hybridize to animal telomeres.

Human DNA was prepared by lysis of monolayers of HeLa cells with 100 mM Tris-HCl pH 8.0, 50 mM EDTA, 500 mM NaCl, 1% SDS, and 100 µg/ml Proteinase K. After incubation for 1 hour, the lysates were phenol-extracted twice and chloroform-extracted once. The genomic DNA was then collected by ethanol precipitation. The *A. thaliana* telomere probe hybridized to both human and *Caenorhabditis elegans* DNA under low stringency conditions, but pAtT4 did not hybridize to the *Drosophila melanogaster* genome.

To test if the pAtT4-cross-hybridizing sequences in the human genome were telomeric, pAtT4 was used to probe a Southern blot (HindIII digest) of Bal31-treated human DNA. FIG. 6A shows that pAtT4 hybridized to a heterodisperse band ranging from 8.5 to 15 kb, in addition to two well-defined higher molecular weight bands of 22 and 45 kb. The 22 and 45 kb band shifted mobility and eventually disappeared with increasing exonuclease digestion. Two faint bands of 2.3 and 3.5 kb are also seen in FIG. 6A, which were not affected by the exonuclease treatment.

As a control, the filter shown in FIG. 6A was stripped and reprobed with a Xenopus rDNA clone which cross-hybridized to human rRNA genes. Restriction fragments carrying the human rRNA genes do not change mobility during the exonuclease treatment, as shown in FIG. 6B.

These data suggest that most of the pAtT4 cross-hybridizing sequences of human DNA are telomeric.

EXAMPLE 17

First Method of Isolation of Autonomous Replicating Sequence

An inverted telomere repeat is integrated into an *A. thaliana* chromosome using the Agrobacterium/T-DNA transformation system. Genes for different drug resistances are placed on either side of the telomere palindrome. After integration of this construct into an *A. thaliana* chromosome, a resolution reaction generates two chromosome fragments, both of which can be selected for by requiring that transformants to be resistant to both drugs. Since the average *A. thaliana* chromosome is only 20 Mb long, random integration of the telomere palindrome leads to the formation of an isolatable ($\leq 1$ Mb) acentric minichromosome in approximately 10% of the transformation events. The isolated minichromosome is further fragmented using in vitro cloning techniques and assayed for extrachromosomal replication in plant cells.

In this way, the sequences comprising a functional plant replication origin may be defined.

EXAMPLE 18

Second Method of Isolation of Autonomous Replicating Sequences

As a first step, a plasmid cloning vector is constructed with the following features: i) a plasmid replication origin and a selectable marker that functions in *E. coli*, ii) a selectable marker that functions in plant cells, iii) a cloning site(s) for insertion of plant genomic DNA fragments, and iv) an *A. thaliana* telomere inverted repeat separated by a stuffer fragment flanked by NotI sites (the stuffer fragment permitted replication of the plasmid as a circle in *E. coli*).

An *A. thaliana* genomic library is then constructed for this cloning vector and maintained in an *E. coli* host. Plasmid DNA prepared from this library is digested with the restriction endonuclease NotI to generate linear molecules with two telomeric ends. These linear DNA are then introduced into plant cells by direct DNA transformation (see Potrykus et al., *Plant Mol. Biol. Rptr.* 3:117-128 (1985)) and the transformants selected.

Introduction of the DNA into plant cells as linear molecules with telomeric ends reduces the frequency of random integration into the chromosomes caused by recombinogenic, broken DNA ends formed during transfection (see, for example, Perrot et al., *Mol. Cell Biol.* 7:1725-1730 (1987). Since extrachromosomally replicating DNA molecules without centromeres are mitotically unstable, screening for transformants which lose the marker under nonselective growth is required (see Hsiao et al., *Proc. Natl. Acad. Sci. USA* 78:3760-3764 (1981)). Once unstable transformants are identified, extrachromosomal DNA is prepared to recover the linear minichromosomes. The ARS sequence responsible for extrachromosomal replication is then identified and studied by mutational analysis.

EXAMPLE 19

Construction of Artificial Plant Chromosomes

Plant artificial chromosomes are constructed by combining the previously isolated essential chromosomal elements. Various configurations of assembled artificial chromosomes are described below for purposes of illustration (see FIG. 10). These artificial chromosomes are designed to be "shuttle vectors"; they can be maintained in a convenient host (either *E. coli* or yeast) as well as plant cells.

An artificial chromosome can be maintained in *E. coli* as a circular molecule by placing a removable stuffer fragment between the telomeric sequence blocks (see FIG. 10(A)). The stuffer fragment is a dispensable DNA sequence, bordered by unique restriction sites, which can be removed by restriction digestion of the circular DNAs to create linear molecules with telomeric ends. In addition to the stuffer fragment and the plant telomeres, the artificial chromosome contains a replication origin and selectable marker that can function in *E. coli* to allow the circular molecules to be maintained in *E. coli* cells. The artificial chromosomes also include a plant selectable marker, a plant centromere, and a plant ARS to allow replication and maintenance of the DNA molecules in plant cells. Finally, the artificial chromosome includes several unique restriction sites where additional DNA sequence inserts can be cloned. The most expeditious method of physically constructing such an artificial chromosome, i.e., ligating the various essential elements together for example, will be apparent to those of ordinary skill in this art.

FIG. 10(B) illustrates an artificial chromosome that can be maintained as a circular molecule in yeast cells. Again, a stuffer fragment is included to separate the telomeric sequence blocks and facilitate the replication of the molecule as a circle. The artificial chromosome also contains a plant selectable marker, a plant centromere, a plant ARS, and cloning sites. To allow maintenance of the DNA molecule in yeast, a yeast ARS, a yeast centromere, and yeast selectable marker are also included.

Alternatively, a plant artificial chromosome is constructed that can be maintained as a linear molecule in yeast by utilizing the *A. thaliana* telomeres as shown in FIG. 10(C).

The instant disclosure sets forth all essential information in connection with the invention. It has been described in some detail by way of illustration and example for purposes of clarity and understanding. It will be obvious that certain changes and modifications may be practiced within the scope of the invention, as limited only by the scope of the appended claims.

What is claimed is:

1. A recombinant DNA construct comprising a telomere, said telomere consisting essentially of tandem repeats of the sequence

5'-CCCTAAA-3' in sufficient quantity to provide a telomere property to a linear double-stranded DNA construct when said telomere is double-stranded and is oriented such that the C-rich 5' end of each tandem repeat is closer to the blunt end of the telomere than the A-rich 3' end of each repeat.

2. The recombinant DNA construct of claim 1, which additionally comprises a yeast centromere.

3. The recombinant construct of claim 1, which additionally comprises a yeast autonomous replicating sequence.

4. The recombinant construct of claim 1, which additionally comprises a selectable marker gene.

5. A recombinant DNA construct comprising a telomere of a higher eukaryotic organism, a yeast centromere, and a yeast autonomous replicating sequence, said telomere consisting essentially of tandem repeats of the sequence

5'-CCCTAAA-3' in sufficient quantity to provide a telomere property to a linear double-stranded DNA construct when said telomere is double-stranded and is oriented such that the C-rich 5' end of each tandem repeat is closer to the blunt end of the telomere than the A-rich 3' end of each repeat.

6. The recombinant DNA construct of claim 5, which additionally comprises a selectable marker gene.

7. The recombinant DNA construct of any one of claims 1 or 4, which is capable of being maintained as a chromosome.

8. A plasmid comprising the recombinant DNA construct of claim 7.

9. The plasmid of claim 8, wherein said plasmid further comprises an origin of replication and a selection marker that function in bacteria.

10. The plasmid of claim 9, wherein said bacteria is *E. coli*.

11. The plasmid of claim 8, wherein said plasmid further comprises an origin of replication and a selection marker that function in yeast.

12. The plasmid of claim 11, wherein said yeast is *S. cerevisiae*.

13. The construct of claim 7, which additionally comprises a desired gene sequence.

14. The construct of claim 13, wherein said desired gene sequence is selected from the group consisting of:
 (1) a gene sequence of a hormone gene;
 (2) a gene sequence of an antibiotic resistance gene;
 (3) a gene sequence of a nitrogen fixation gene;
 (4) a gene sequence of a plant pathogen defense gene;
 (5) a gene sequence of a plant stress-induced gene;
 (6) a gene sequence of a toxin gene; and
 (7) a gene sequence of a seed storage gene.

15. The construct of claim 14, wherein said construct is capable of expressing said desired gene sequence.

16. The construct of claim 14, wherein said construct is capable of expressing said desired gene in a prokaryote.

17. The construct of claim 14, wherein said construct is capable of expressing said desired gene in a eukaryote.

18. The construct of claim 17, wherein said eukaryote is a higher eukaryote.

19. The construct of claim 18, wherein said higher eukaryote is a plant.

20. A recombinant DNA construct comprising the pAtT4 plasmid, Accession Number ATCC 67577.

21. A recombinant DNA construct comprising the sequence of FIG. 4.

22. A host cell transformed with the recombinant DNA construct of any one of claims 1 or 5.

23. The host cell of claim 22, which is a eukaryotic cell.

24. The host cell of claim 23, which is a higher eukaryotic cell.

25. The host cell of claim 24, which is a plant cell.

* * * * *

UNITED STATES PATENT AND TRADEMARK OFFICE
CERTIFICATE OF CORRECTION

PATENT NO. : 5,270,201

DATED : December 14, 1993

INVENTOR(S) : Richards, et al

Page 1 of 2

It is certified that error appears in the above-indentified patent and that said Letters Patent is hereby corrected as shown below:

Title page, under the heading "Other Publications" Column 1, line 40, delete "104(9)", and insert therein --174(9)--; delete "Babel", and insert therein --Zabel--; line 27, delete "plants" and insert therein --plant--. Page 1, under the heading "Other Publications" Column 2, line 2, delete "(1900)" and insert therein --(1990)--. Column 4, line 24, delete "corresponding" and insert therein --correspondingly--. Column 7, line 50, delete "Hinc11" and insert therein --HincII--. Column 9, line 29, between "FIG 16" and "shows", insert --(A-C)--. Column 11, line 37, delete "wellknown", and insert therein --well-known--. Column 13, line 27, delete "Drosphila" and insert therein --*Drosophila*--. Column 19, line 60, delete "Biochmeical" and insert therein --Biochemical--. Column 20, line 12, delete "Hybridization" and insert therein --Hybridizations--; Column 20, line 23, delete "(1097)" and insert therein --(1987)--. Column 21, line 11, delete "DBA" and insert therein --DNA--. Column 22, line 39, delete "I" and insert therein --1--. Column 24, line 4, delete "Hinc11" and insert therein --HincII--; Column 24, line 46, delete "clones", and insert therein --clone--. Column 25, line 56, delete "silbings" and insert therein --siblings--. Column 30, line 56, delete "repeats" and insert therein, --repeat--. Column 31, line 43, delete "Cross-Hybridation" and insert therein, --Cross-Hybridization--. Column 32, line 22, between the words "transformants" and "be" delete the word "to".

UNITED STATES PATENT AND TRADEMARK OFFICE
CERTIFICATE OF CORRECTION

PATENT NO. : 5,270,201
DATED : December 14, 1993
INVENTOR(S) : Richards, et al

It is certified that error appears in the above-indentified patent and that said Letters Patent is hereby corrected as shown below:

Column 33, line 43, between the words "and" and "yeast" insert the word "a". Column 34, line 23, (Claim 7, line 2), delete "1 or 4" and insert therein --1,2,3,4 or 5--.

Signed and Sealed this

Eighteenth Day of October, 1994

Attest:

BRUCE LEHMAN

*Attesting Officer*     *Commissioner of Patents and Trademarks*